United States Patent
Roe et al.

(10) Patent No.: US 9,220,637 B2
(45) Date of Patent: Dec. 29, 2015

(54) DISPOSABLE ABSORBENT ARTICLES WITH ZONES COMPRISING ELASTOMERIC COMPONENTS

(75) Inventors: Donald Carroll Roe, West Chester Township, OH (US); Fred Naval Desai, Fairfield, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 765 days.

(21) Appl. No.: 11/953,287

(22) Filed: Dec. 10, 2007

(65) Prior Publication Data

US 2008/0103473 A1 May 1, 2008

Related U.S. Application Data

(62) Division of application No. 11/077,779, filed on Mar. 11, 2005, now abandoned.

(60) Provisional application No. 60/557,288, filed on Mar. 29, 2004.

(51) Int. Cl.
*A61F 13/494* (2006.01)
*A61F 13/15* (2006.01)
(Continued)

(52) U.S. Cl.
CPC ....... *A61F 13/15203* (2013.01); *A61F 13/4902* (2013.01); *A61F 13/496* (2013.01); *A61F 13/49012* (2013.01); *A61F 13/49015* (2013.01); *A61F 13/5622* (2013.01); *A61F 2013/49026* (2013.01); *A61F 2013/49028* (2013.01)

(58) Field of Classification Search
CPC ................... A61F 13/49012; A61F 13/49017; A61F 13/49019

USPC ................. 604/385.26–385.27, 396, 385.04, 604/385.24, 385.25

See application file for complete search history.

(56) References Cited

U.S. PATENT DOCUMENTS 2,413,970 A   1/1947   Hawley, Jr.
2,866,459 A * 12/1958  Sobelson ...................... 604/377
(Continued)

FOREIGN PATENT DOCUMENTS

DE   19516037 A1   11/1996
EP   0 472 942 B1   9/1995
(Continued)

OTHER PUBLICATIONS

Greg Hearn, Multistrand Elastics' Role in Diaper Performance, Nonwovens World, Apr.-May 2003, pp. 63-68.
(Continued)

*Primary Examiner* — Tan-Uyen (Jackie) T Ho
*Assistant Examiner* — Paula L Craig
(74) *Attorney, Agent, or Firm* — Sarah M. DeCristofaro; Abbey A. Lopez; Charles R. Ware

(57) ABSTRACT

Absorbent articles having a liquid permeable topsheet, a liquid impermeable backsheet, and an absorbent core disposed between said topsheet and said backsheet are disclosed. The absorbent articles include a thermoplastic elastomer joined to or disposed in a stretch zone on at least one component or region of the absorbent article to impart an elastic resistance that provides sizing or shaping capabilities to the article. The absorbent article can be in the form of diapers, pull-on diapers, training pants, sanitary napkins, wipes, bibs, incontinence briefs or inserts.

19 Claims, 22 Drawing Sheets

(51) Int. Cl.
*A61F 13/496* (2006.01)
*A61F 13/56* (2006.01)
*A61F 13/49* (2006.01)

(56) References Cited

U.S. PATENT DOCUMENTS

| | | | |
|---|---|---|---|
| 3,848,594 A | 11/1974 | Buell | |
| 3,860,003 A | 1/1975 | Buell | |
| 4,322,467 A | 3/1982 | Heimbach et al. | |
| 4,323,070 A * | 4/1982 | Ternstrom et al. | 604/385.25 |
| 4,342,314 A | 8/1982 | Radel et al. | |
| 4,515,595 A | 5/1985 | Kievit et al. | |
| 4,610,678 A | 9/1986 | Weisman et al. | |
| 4,662,875 A | 5/1987 | Hirotsu et al. | |
| 4,673,402 A | 6/1987 | Weisman et al. | |
| 4,695,278 A | 9/1987 | Lawson | |
| 4,699,622 A | 10/1987 | Toussant et al. | |
| 4,705,584 A | 11/1987 | Lauchenauer | |
| 4,834,735 A | 5/1989 | Alemany et al. | |
| 4,846,815 A | 7/1989 | Scripps | |
| 4,888,231 A | 12/1989 | Angstadt | |
| 4,892,536 A | 1/1990 | DesMarais et al. | |
| 4,894,060 A | 1/1990 | Nestegard | |
| 4,940,464 A | 7/1990 | Van Gompel et al. | |
| 4,946,527 A | 8/1990 | Battrell | |
| 4,963,140 A | 10/1990 | Robertson et al. | |
| 4,990,147 A | 2/1991 | Freeland | |
| 5,037,416 A | 8/1991 | Allen et al. | |
| 5,055,103 A | 10/1991 | Nomura et al. | |
| 5,057,097 A | 10/1991 | Gesp | |
| 5,092,861 A | 3/1992 | Nomura et al. | |
| 5,137,537 A | 8/1992 | Herron et al. | |
| 5,147,345 A | 9/1992 | Young et al. | |
| 5,151,092 A | 9/1992 | Buell | |
| 5,156,793 A | 10/1992 | Buell et al. | |
| 5,167,897 A | 12/1992 | Weber et al. | |
| 5,217,798 A | 6/1993 | Brady et al. | |
| 5,221,274 A | 6/1993 | Buell | |
| 5,236,430 A | 8/1993 | Bridges | |
| 5,242,436 A | 9/1993 | Weil et al. | |
| 5,246,433 A | 9/1993 | Hasse et al. | |
| 5,260,345 A | 11/1993 | DesMarais et al. | |
| 5,269,775 A | 12/1993 | Freeland et al. | |
| 5,302,454 A | 4/1994 | Cecchin et al. | |
| 5,330,598 A | 7/1994 | Erdman et al. | |
| 5,342,338 A | 8/1994 | Roe | |
| 5,368,584 A | 11/1994 | Clear et al. | |
| 5,385,775 A * | 1/1995 | Wright | 442/183 |
| 5,387,207 A | 2/1995 | Dyer et al. | |
| 5,397,316 A | 3/1995 | LaVon et al. | |
| 5,447,508 A * | 9/1995 | Numano et al. | 604/385.27 |
| 5,449,353 A * | 9/1995 | Watanabe et al. | 604/385.27 |
| H1517 H | 2/1996 | Erickson et al. | |
| 5,499,978 A | 3/1996 | Buell et al. | |
| 5,507,736 A | 4/1996 | Clear et al. | |
| 5,542,942 A | 8/1996 | Kline et al. | |
| 5,547,736 A | 8/1996 | Simon et al. | |
| 5,554,143 A | 9/1996 | Roe et al. | |
| 5,554,144 A | 9/1996 | Roe et al. | |
| 5,554,145 A | 9/1996 | Roe et al. | |
| 5,556,394 A | 9/1996 | Roe et al. | |
| 5,569,232 A | 10/1996 | Roe et al. | |
| 5,569,234 A | 10/1996 | Roe et al. | |
| 5,571,096 A | 11/1996 | Dobrin et al. | |
| 5,575,783 A | 11/1996 | Clear et al. | |
| 5,580,411 A | 12/1996 | Nease et al. | |
| 5,591,152 A | 1/1997 | Buell et al. | |
| 5,594,080 A | 1/1997 | Waymouth et al. | |
| 5,650,222 A | 7/1997 | DesMarais et al. | |
| 5,662,758 A | 9/1997 | Hamilton et al. | |
| 5,669,897 A | 9/1997 | Lavon et al. | |
| 5,671,678 A | 9/1997 | Bolte et al. | |
| 5,735,839 A * | 4/1998 | Kawaguchi et al. | 604/385.29 |
| 5,749,865 A | 5/1998 | Yamamoto et al. | |
| 5,749,866 A | 5/1998 | Roe et al. | |
| H1750 H | 9/1998 | Dobrin | |
| 5,858,012 A * | 1/1999 | Yamaki et al. | 604/385.27 |
| 5,865,823 A | 2/1999 | Curro | |
| 5,871,607 A | 2/1999 | Hamilton et al. | |
| 5,876,391 A | 3/1999 | Roe et al. | |
| 5,876,392 A * | 3/1999 | Hisada | 604/385.29 |
| 5,897,545 A | 4/1999 | Kline et al. | |
| 5,904,673 A | 5/1999 | Roe et al. | |
| 5,910,224 A | 6/1999 | Morman | |
| 5,916,206 A * | 6/1999 | Otsubo et al. | 604/385.27 |
| 5,916,663 A | 6/1999 | Chappell et al. | |
| 5,941,865 A * | 8/1999 | Otsubo et al. | 604/385.29 |
| 5,957,908 A | 9/1999 | Kline et al. | |
| 5,997,521 A | 12/1999 | Robles et al. | |
| 6,004,306 A | 12/1999 | Robles et al. | |
| 6,050,985 A | 4/2000 | Lavon et al. | |
| 6,056,732 A * | 5/2000 | Fujioka et al. | 604/385.01 |
| 6,107,537 A | 8/2000 | Elder et al. | |
| 6,120,487 A | 9/2000 | Ashton | |
| 6,120,489 A | 9/2000 | Johnson et al. | |
| 6,132,409 A | 10/2000 | Vogt et al. | |
| 6,168,584 B1 | 1/2001 | Allen et al. | |
| 6,179,820 B1 * | 1/2001 | Fernfors | 604/385.27 |
| 6,193,701 B1 | 2/2001 | Van Gompel et al. | |
| 6,193,918 B1 | 2/2001 | McGuire et al. | |
| 6,245,050 B1 | 6/2001 | Odorzynski et al. | |
| 6,264,643 B1 * | 7/2001 | Toyoda | 604/385.29 |
| 6,303,208 B1 | 10/2001 | Pelkie | |
| 6,306,122 B1 * | 10/2001 | Narawa et al. | 604/385.3 |
| 6,313,372 B1 | 11/2001 | Suzuki | |
| 6,325,787 B1 | 12/2001 | Roe et al. | |
| 6,364,863 B1 * | 4/2002 | Yamamoto et al. | 604/385.27 |
| 6,409,858 B1 * | 6/2002 | Popp et al. | 156/66 |
| 6,429,352 B1 | 8/2002 | Herrlein et al. | |
| 6,432,098 B1 | 8/2002 | Kline et al. | |
| 6,436,512 B1 | 8/2002 | Kauschke et al. | |
| 6,448,464 B1 | 9/2002 | Akin et al. | |
| 6,465,073 B1 | 10/2002 | Morman et al. | |
| 6,478,785 B1 | 11/2002 | Ashton et al. | |
| 6,495,229 B1 | 12/2002 | Carte et al. | |
| 6,503,236 B1 | 1/2003 | Uitenbroek et al. | |
| 6,531,025 B1 | 3/2003 | Lender et al. | |
| 6,531,027 B1 | 3/2003 | Lender et al. | |
| 6,552,245 B1 | 4/2003 | Roessler et al. | |
| 6,585,713 B1 | 7/2003 | LeMahieu et al. | |
| 6,595,976 B2 * | 7/2003 | Jitoe et al. | 604/385.29 |
| 6,620,146 B2 * | 9/2003 | Gibbs | 604/385.3 |
| 6,623,468 B2 | 9/2003 | Shimoe | |
| 6,677,038 B1 | 1/2004 | Topolkaraev et al. | |
| 6,680,265 B1 | 1/2004 | Smith et al. | |
| 6,682,514 B1 | 1/2004 | Brunner | |
| 6,686,303 B1 | 2/2004 | Haynes et al. | |
| 6,703,537 B1 | 3/2004 | Roe et al. | |
| 6,827,806 B2 | 12/2004 | Uitenbroek et al. | |
| 6,833,179 B2 | 12/2004 | May et al. | |
| 6,875,710 B2 | 4/2005 | Eaton et al. | |
| 6,878,647 B1 * | 4/2005 | Rezai et al. | 442/18 |
| 6,896,843 B2 | 5/2005 | Topolkaraev et al. | |
| 6,939,334 B2 | 9/2005 | Odorzynski et al. | |
| 6,994,761 B2 | 2/2006 | Klemp et al. | |
| 7,291,138 B2 * | 11/2007 | Hoshino et al. | 604/385.27 |
| 7,331,946 B2 * | 2/2008 | Shimada et al. | 604/385.3 |
| 9,033,947 B2 * | 5/2015 | Roe et al. | 604/385.27 |
| 2001/0049516 A1 * | 12/2001 | Shimada et al. | 604/385.11 |
| 2002/0002021 A1 | 1/2002 | May et al. | |
| 2002/0007164 A1 | 1/2002 | Boggs et al. | |
| 2002/0009940 A1 | 1/2002 | May et al. | |
| 2002/0045877 A1 * | 4/2002 | Shimada et al. | 604/385.29 |
| 2002/0123730 A1 * | 9/2002 | Popp et al. | 604/385.03 |
| 2002/0128617 A1 | 9/2002 | Roe et al. | |
| 2002/0165518 A1 * | 11/2002 | Datta et al. | 604/385.29 |
| 2002/0165097 A1 | 12/2002 | Giachetto et al. | |
| 2003/0018315 A1 * | 1/2003 | Popp et al. | 604/386 |
| 2003/0083635 A1 | 5/2003 | Gibbs | |
| 2003/0084996 A1 | 5/2003 | Alberg et al. | |
| 2003/0087059 A1 | 5/2003 | Jackson et al. | |
| 2003/0087098 A1 | 5/2003 | Eaton et al. | |
| 2003/0088220 A1 | 5/2003 | Molander et al. | |
| 2003/0088228 A1 | 5/2003 | Desai et al. | |

(56) References Cited

U.S. PATENT DOCUMENTS

| | | |
|---|---|---|
| 2003/0091807 A1 | 5/2003 | Desai et al. |
| 2003/0100879 A1* | 5/2003 | Kline et al. .................. 604/386 |
| 2003/0109842 A1* | 6/2003 | Louis et al. .............. 604/385.29 |
| 2003/0153894 A1 | 8/2003 | Gibbs et al. |
| 2003/0204017 A1 | 10/2003 | Stevens et al. |
| 2003/0233082 A1 | 12/2003 | Kline et al. |
| 2004/0005835 A1* | 1/2004 | Zhou et al. .................. 442/328 |
| 2004/0006324 A1* | 1/2004 | Zhou et al. .............. 604/385.24 |
| 2004/0019139 A1 | 1/2004 | Hanke et al. |
| 2004/0024109 A1 | 2/2004 | Hamersky et al. |
| 2004/0044323 A1 | 3/2004 | Roessler et al. |
| 2004/0049836 A1 | 3/2004 | Ashraf et al. |
| 2004/0078018 A1 | 4/2004 | Gompel et al. |
| 2004/0083958 A1* | 5/2004 | Saidman et al. ............... 118/688 |
| 2004/0087235 A1 | 5/2004 | Morman et al. |
| 2004/0106723 A1 | 6/2004 | Yang et al. |
| 2004/0110442 A1 | 6/2004 | Rhim et al. |
| 2004/0122408 A1 | 6/2004 | Potnis et al. |
| 2004/0122409 A1 | 6/2004 | Thomas et al. |
| 2004/0126579 A1 | 7/2004 | Creagan |
| 2004/0127128 A1 | 7/2004 | Thomas |
| 2004/0127131 A1 | 7/2004 | Potnis |
| 2004/0127881 A1 | 7/2004 | Stevens et al. |
| 2004/0134596 A1 | 7/2004 | Rosati et al. |
| 2004/0142110 A1 | 7/2004 | Branca et al. |
| 2004/0192140 A1* | 9/2004 | Schneider et al. ............ 442/329 |
| 2005/0075618 A1* | 4/2005 | Kenmochi et al. ....... 604/385.27 |
| 2005/0096416 A1* | 5/2005 | Zhou et al. .................. 524/270 |
| 2005/0096624 A1* | 5/2005 | Hoshino et al. .......... 604/385.27 |
| 2005/0211368 A1 | 9/2005 | McGuire et al. |
| 2005/0215963 A1 | 9/2005 | Autran et al. |
| 2005/0215970 A1 | 9/2005 | Kline et al. |
| 2005/0215972 A1* | 9/2005 | Roe et al. ................. 604/385.29 |
| 2005/0215973 A1 | 9/2005 | Roe et al. |

FOREIGN PATENT DOCUMENTS

| | | |
|---|---|---|
| EP | 0 745 433 B1 | 12/1996 |
| EP | 1 081 672 A2 | 3/2001 |
| EP | 1 184 012 A1 | 3/2002 |
| EP | 1 197 195 A1 | 4/2002 |
| JP | 04-371148 A | 12/1992 |
| JP | 07 089012 | 8/1995 |
| JP | 10 53963 | 2/1998 |
| JP | 2001-157690 A | 6/2001 |
| WO | WO 94/01507 A1 | 1/1994 |
| WO | WO 95/16746 A1 | 6/1995 |
| WO | WO 96/24485 A1 | 8/1996 |
| WO | WO 97/47264 A1 | 12/1997 |
| WO | WO 01/27373 A1 | 4/2001 |
| WO | WO 03/037237 | 5/2003 |
| WO | WO 03/039421 A2 | 5/2003 |
| WO | WO 2007/103097 A1 | 9/2007 |

OTHER PUBLICATIONS

European Search Report, dated Feb. 17, 2009, Appl. No./Pat. No. 08101562.0-2124 / 1964534.

European Search Report, dated Feb. 23, 2009, Appl. No./Pat. No. 08101561.2-2124 / 1964533.

\* cited by examiner

DISPOSABLE ABSORBENT ARTICLES WITH ZONES COMPRISING ELASTOMERIC COMPONENTS

CROSS REFERENCE TO RELATED APPLICATIONS

This application is a divisional of U.S. application Ser. No. 11/077,779, filed Mar. 11, 2005 now abandoned, which claims the benefit of U.S. Provisional Application No. 60/557,288, filed Mar. 29, 2004, the substances of which are incorporated herein by reference.

FIELD OF THE INVENTION

The present invention generally relates to disposable absorbent articles such as diapers, pull-on diapers, training pants, sanitary napkins, wipes, bibs, incontinence briefs or inserts and the like. More specifically, the invention is directed to such absorbent articles that have one or more regions comprising an elastomeric component. Such components are used in the absorbent articles of the invention to provide the desired article shape and/or to impart the desired stress and strain properties for improved fit and comfort of the article on the wearer and/or for increased convenience of the user.

BACKGROUND OF THE INVENTION

Disposable absorbent products, such as diapers, training pants, incontinence articles typically include stretchable materials, such as elastic strands, in the waist region and the cuff regions to provide a snug fit and a good seal of the article. Pant-type absorbent articles further include stretchable materials in the side portions for easy application and removal of the article and for sustained fit of the article. Stretchable materials have also been used in the ear portions of disposable diapers for adjustable fit of the article. However, it would be desirable to have materials with improved properties that better define directionality and intensity of the tensile forces provided by the contractive portions of the absorbent article. In this way, such desirable absorbent articles would have the ability to shape or size to the wearer for better fit and comfort, yet have the ability to maintain the required tension when on a wearer to achieve sustained fit and prevent sagging and/or drooping of the article. Absorbent articles of this kind would result in better fit in various areas of the absorbent article, e.g., the crotch or waist region of a diaper with resulting improvements in comfort. In the case of a diaper, better fit and comfort can also impart better functional performance such as reduced leakage since the diaper would better conform to the shape of a wearer. Such features have heretofore not been available for absorbent articles.

There are various approaches to providing desirable stretchable properties in targeted areas of absorbent articles. Stretchable materials may be strands, films or nonwoven fibrous webs made of elastomeric materials. Typically, such materials are stretchable in at least one, and possibly multiple, directions. However, because the films or webs are made entirely of elastomeric materials, they are relatively expensive, and they tend to have more drag on skin surface, resulting in discomfort to the wearer of the article. Sometimes, the stretchable strands or films are laminated to one or more layers of nonwoven webs. Since typical nonwoven webs typically are made of thermoplastic fibers, they have very limited stretchability and, the resulting laminates provide considerable resistance to stretch. It is necessary to reduce this resistance substantially in order to make functional stretch laminates. However, such materials do not have sufficient ability to shape, size or conform to the particularities of the wearer's anatomy upon application.

Other approaches to make stretchable materials are also known, such as stretch-bonded laminates and neck-bonded laminates. Stretch bonded laminates are made by stretching an elastic strand in the machine direction (MD), laminating it to a nonwoven substrate while it is in the stretched state, and releasing the applied tension so that the nonwoven gathers and takes on a puckered shape. Neck-bonded laminates are made by first stretching the nonwoven substrate in the machine direction such that it necks (i.e., reduces its CD dimension) then bonding CD oriented elastic strands to the substrate while the substrate is still in the stretched, necked state. This laminate will be stretchable in the CD, at least up to the original width of the nonwoven before it was necked. Combinations of stretch bonding and neck bonding have also been known to deliver stretch in both MD and CD directions. In these approaches, at least one of the components is in a tensioned (i.e., stretched) state when the components of the laminates are joined together. Again, these materials cannot be effectively used in absorbent articles to impart the desired sizing or shaping features desired by users and wearers of absorbent articles.

Zero strain stretch laminates are also known. The zero strain stretch laminates are made by bonding an elastomer to a nonwoven while both are in an unstrained state. The laminates are then incrementally stretched to impart the stretch properties. The incrementally stretched laminates are stretchable only to the extent afforded by the non-recovered (i.e., residual) extensibility of the laminate. For example, U.S. Pat. No. 5,156,793 discloses a method for incrementally stretching an elastomer-nonwoven laminate, in a non-uniform manner, to impart elasticity to the resulting laminate. These stretch laminates behave similar to the materials described previously in that they do not have sufficient ability to size or shape to the wearer.

However, in all the approaches above, the materials or laminates are made separately and then incorporated into the absorbent article. For example, the stretch laminates described herein may be cut into the appropriate size and shape, then attached to the desired location in the product in a process sometimes referred as the "cut-and-slip" process. Because of the different stretch properties required for different elements of the product, it is necessary to make a variety of laminates having different stretchability and cut the laminates to different sizes and shapes. Several cut-and-slip units may be needed to handle the different stretchability of the stretch laminates and to attach them to different locations of the product. As the number of cut-and-slip units and/or steps multiplies, the process quickly becomes cumbersome, complicated and expensive. These processes are suitable for modern day absorbent article manufacture and are desirable. However, it would also be desirable to have absorbent articles having the desired sizing and/or shaping properties, but which can be disposed in or on the absorbent article without the need for such complicated and expensive "cut-and-slip" processes.

One alternative to cut and slip processes used by the art is to print an elastomeric composition onto a substrate. Exemplary disclosures include U.S. Pat. No. 6,531,027 which discusses adhering components of an absorbent article using an adhesive printing process, PCT Application No. 03/039420 which discusses printing first and second elastomeric compositions onto a substrate where the compositions differ in at least one of the following properties: elasticity, melt viscosity, composition, shape, pattern, add-on level, and PCT Application No. WO 03/053308, which discusses printing an elastic adhesive onto an extendable substrate to provide a tensioning force during garment wear.

Based on the foregoing, it would be desirable to have absorbent articles with stretchable material having elastic properties such that it can be extended as desired but still retains the desired degree of elasticity to facilitate sustained fit on the wearer. It would also be desirable to have such a material that can be disposed easily on any specific area of the absorbent article, or component thereof in any desired amount. Additionally, it would be desirable to have such a material or composite having elastic properties that can be easily placed in discrete, spaced apart areas of the absorbent article or a component thereof via known deposition techniques such as printing (including gravure, offset, letterpress and screen techniques), extrusion coating, roll coating and the like.

SUMMARY OF THE INVENTION

The aforementioned needs in the art are met by the present invention which provides an absorbent article with a material that has elastic properties disposed in a predetermined pattern defining a stretch zone that provides desired elastic directionality and intensity to specific regions of the absorbent article. Such directionality and intensity is controlled by controlling the amount, placement and orientation of a thermoplastic elastomer that is disposed only on certain zones or regions of the absorbent article or a component thereof.

In accordance with one aspect of the invention, an absorbent article is provided that comprises a liquid permeable topsheet, a liquid impermeable backsheet, and an absorbent core disposed between the topsheet and the backsheet. The article may also include additional features such as one or more ears or side panels, leg cuffs, and fastener components, elastic belts. In other aspects of the invention, the material used in the absorbent article is provided with one or more stretch zones where the stretch zones may comprise at least a portion of one or more of the features. In another embodiment of the invention a plurality of the stretch zones are assembled into an array thereof.

DETAILED DESCRIPTION OF THE INVENTION

Definitions

Figure 1:
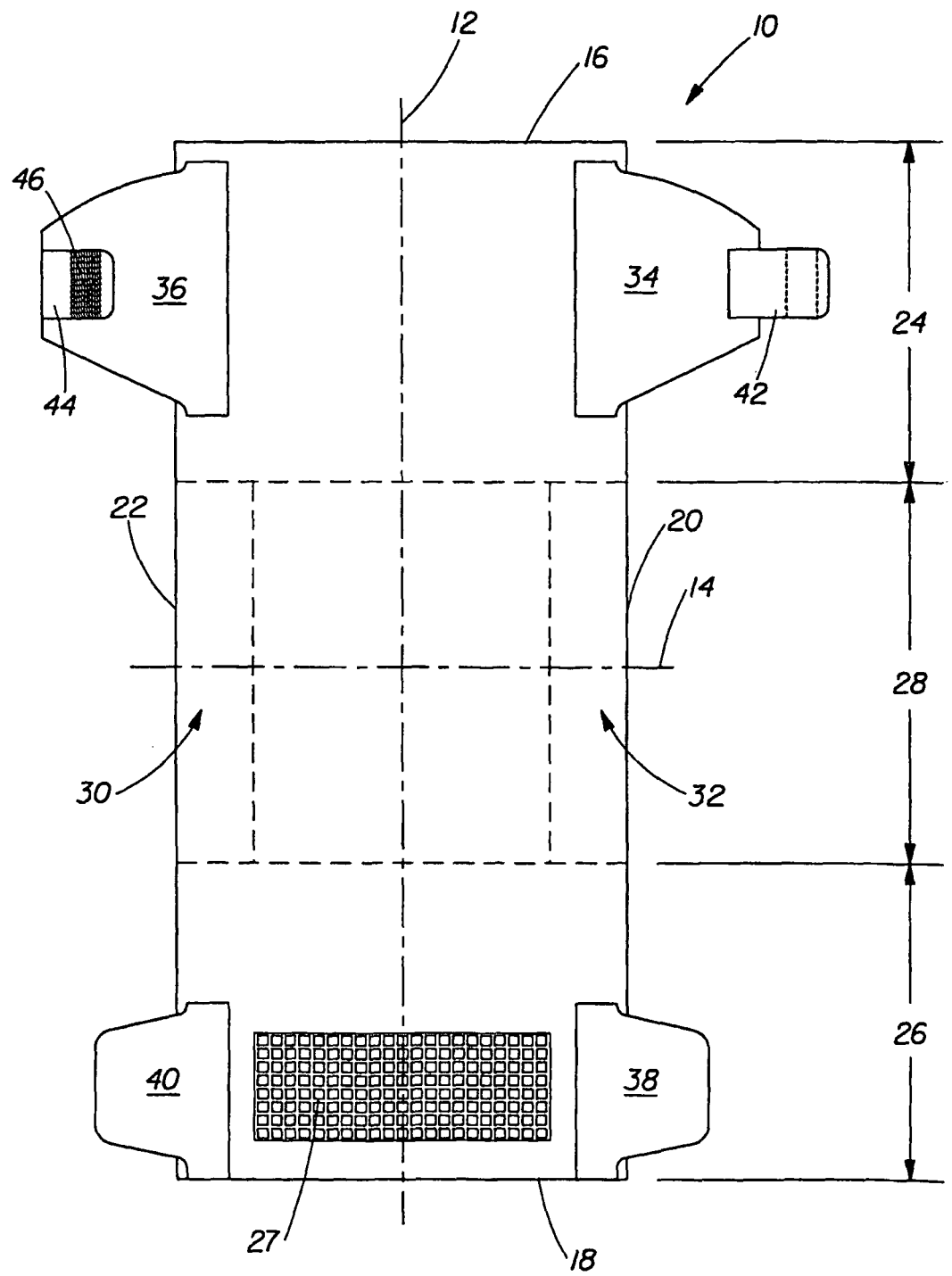
FIG. 1 is a plan view of a diaper in accordance with the invention.

The term "disposable" is used herein to describe absorbent articles that generally are not intended to be laundered or otherwise restored or reused as an absorbent article (i.e., they are intended to be discarded after a single use and, preferably, to be recycled, composted or otherwise disposed of in an environmentally compatible manner).

As used herein, the term "disposed" is used to mean that an element(s) is formed (joined and positioned) in a particular place or position as a unitary structure with other elements or as a separate element joined to another element.

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.

A "unitary" absorbent article refers to absorbent articles which are formed of separate parts united together to form a coordinated entity so that they do not require separate manipulative parts like a separate holder and liner.

As used herein, the term "diaper" refers to an absorbent article generally worn by infants and incontinent persons about the lower torso.

By "stretch", it is meant that the material has the ability to extend beyond its original length in at least one dimension when subjected to a tensile force (i.e., tension) applied in the direction of that dimension. "Stretch" may be unidirectional, bi-directional, or multi-directional. The specific "stretch" properties of a material may vary along any of the stretch vectors. As used herein, stretch includes both plastic and elastic deformation.

The term "elastic" or "elastomeric" as used herein refers to any material that upon application of a biasing force, can stretch to an elongated length of at least about 125 percent of its relaxed, original length, without rupture or breakage, and upon release of the applied force, recovers at least about 40% of its elongation, preferably recovers at least 60% of its original length, most preferably recovers about 80% of its original length.

The term "inelastic" refers herein to any material that does not fall within the definition of "elastic" above.

As used herein, the term elastic resistance describes an elastic force that tends to resist an applied tensile force causing a material provided therewith to tend to contract to an untensioned configuration in response to a stretching force.

Elastic resistance is conveniently measured using the method described in the TEST METHODS section below.

"Longitudinal" is a direction running parallel to the maximum linear dimension of the article and includes directions within ±45° of the longitudinal direction. The "lateral" or "transverse" direction is orthogonal to the longitudinal direction. The "Z-direction" is orthogonal to both the longitudinal and transverse directions. The "x-y plane" refers to the plane congruent with the longitudinal and transverse directions.

As used herein, the term "impermeable" generally refers to articles and/or elements that are substantially not penetrated by aqueous fluid through the entire Z-directional thickness thereof under a pressure of 1.0 kPa or less. Preferably, the impermeable article or element is not penetrated by aqueous fluid under pressures of 3.4 kPa or less. More preferably, the impermeable article or element is not penetrated by fluid under pressures of 6.8 kPa or less. An article or element that is not impermeable is permeable.

The term "substrate" as used herein refers to any material, including a film, an apertured film, a nonwoven web, a woven web, a foam or a combination thereof, or a cellulosic material including wood pulp, derivatized or modified cellulosic materials, and the like, having a single layer or multiple layers. The term "fibrous substrate" as used herein refers to a material comprised of a multiplicity of fibers that could be either a natural or synthetic material or any combination thereof, including, for example, nonwoven materials, woven materials, knitted materials, and any combinations thereof.

The term "nonwoven" as used herein refers to a fabric made from continuous filaments and/or discontinuous fibers. Nonwoven fabrics include those made by carding staple fibers, airlaying or wet laying staple fibers and via extrusion processes such as spunbonding and melt blowing. The nonwoven fabric can comprise one or more nonwoven layers, wherein each layer can include continuous filaments or discontinuous fibers. Nonwovens can also comprise bi-component fibers, which can have shell/core, side-by-side, or other known fiber structures.

By "stretch zone", it is meant a portion of a region of an absorbent article having elastic stretch properties. A stretch zone may extend throughout an entire region or feature of the article, extend across multiple regions or features, or comprise merely a portion of, one or more regions or features of the article. A region or feature may also comprise an array of individual stretch zones.

The term "Line of Force" describes the pathway through a web material or structure comprising such web material that is substantially parallel to its surface, that connects two points, zones, or features in the material, and that carries most of the tension when tension is imposed between those two points, zones, or features. The term also applies to pluralities of pathways of close enough proximity, properties, and direction that they effectively behave as a single pathway. The shape, width, and stress/strain behavior of the pathway can be controlled by modifying the stress/strain properties of the material in the desired location and direction of the pathway to produce a higher effective modulus in the pathway compared to areas adjacent to the pathway. The proportion of the tension carried by the pathway depends on the difference in effective modulus between the pathway and the adjacent material. It should be understood that a line of force may be defined by any of the stretch element geometries disclosed herein.

Preferred Embodiments

In accordance with one aspect of the invention, an absorbent article is provided that comprises a liquid permeable topsheet, a liquid impermeable backsheet, and an absorbent core disposed between the topsheet and the backsheet. The article may also include one or more features such as, but not limited to, ears or side panels, leg cuffs, fastener components, and/or a belt. The absorbent article according to present invention is also provided with one or more stretch zones. In most cases such stretch zones will comprise at least a portion of the aforementioned features. In other aspects of the invention, the stretch zones comprise a substrate having an elastomeric composition disposed thereon. The elastomeric composition provides an elastic resistance to the stretch zone upon elongation of at least a portion of the stretch zone. In preferred embodiments of the present invention, the elastomeric composition is disposed on the substrate in a predetermined geometric pattern (i.e., shape and orientation) so as to provide such elastic resistance in a manner that enhances the performance of the feature. The pattern preferably allows the stretch zone to more efficiently carry anchoring loads and tensile forces induced by application of the article to the wearer and/or accommodate movement of the wearer, and/or the weight of the article or waste contents of the article than a typical non-patterned design.

Suitably, an absorbent article according to the present invention must comprise at least one stretch zone wherein the stretch zone comprises an elastomeric composition that is disposed on a substrate so as to at least partially penetrate the substrate. The area of a stretch zone comprises at least the portion of the substrate that is covered by the elastomeric composition. Typically, such stretch zones have the following properties: (1) an elastic resistance (i.e., the load at 25% strain) of at least about 0.05 N/cm, preferably from 0.05 N/cm to about 50 N/cm, more preferably from about 0.05 N/cm to about 40 N/cm, and most preferably from 0.25 N/cm to about 30 N/cm; (2) a percent set of less than about 15%, preferably less than about 12% and more preferably less than about 10%; and (3) a stress relaxation value of less than about 40%, preferably less than about 30%, and more preferably less than about 25%. Methods for measuring these properties are given in the TEST METHODS section below.

In some embodiments an absorbent article may comprise stretch zones that are associated so as to provide an array thereof. Such an array may be disposed on only one region or feature of the absorbent article or may extend across two or more regions or features. The array can comprise intersecting or non-intersecting stretch zones. Also, the stretch zones in the array can either be parallel to one another or form a non-zero angle with respect to each other. When the stretch zones in an array are non-intersecting, individual stretch zones are cut off and their properties may be measured. However, when the stretch zones intersect within an array, it is not possible to separate individual stretch zones. In such cases, the array should be sampled and evaluated as described in the TEST METHODS section below.

Suitable elastomeric compositions comprise thermoplastic elastomers selected from the group consisting of styrenic block copolymers, metallocene-catalyzed polyolefins, polyesters, polyurethanes, polyether amides, and combinations thereof. Suitable styrenic block copolymers may be diblock, triblock, tetrablock, or other multi-block copolymers having at least one styrenic block. Exemplary styrenic block copolymers include styrene-butadiene-styrene, styrene-isoprene-styrene, styrene-ethylene/butylenes-styrene, styrene-ethylene/propylene-styrene, and the like. Commercially available styrenic block copolymers include KRATON® from the Shell Chemical Company of Houston, Tex.; SEPTON® from Kuraray America, Inc. of New York, N.Y.; and VECTOR® from Dexco Chemical Company of Houston, Tex. Commercially available metallocene-catalyzed polyolefins include EXXPOL® and EXACT® from Exxon Chemical Company of Baytown, Tex.; AFFINITY® and ENGAGE® from Dow Chemical Company of Midland, Mich. Commercially available polyurethanes include ESTANE® from Noveon, Inc., Cleveland, Ohio. Commercial available polyether amides include PEBAX® from Atofina Chemicals of Philadelphia, Pa. Commercially available polyesters include HYTREL® from E. I. DuPont de Nemours Co., of Wilmington, Del.

The elastomeric composition may further comprise processing aids and/or processing oils to adjust the melt viscosity of the compositions to the desired range. They include the conventional processing oils, such as mineral oil, as well as other petroleum-derived oils and waxes, such as paraffinic oil, naphthenic oil, petrolatum, microcrystalline wax, paraffin or isoparaffin wax. Synthetic waxes, such as Fischer-Tropsch wax; natural waxes, such as spermaceti, carnauba, ozokerite, beeswax, candelilla, paraffin, ceresin, esparto, ouricury, rezowax, and other known mined and mineral waxes, are also suitable for use herein. Olefinic or diene oligomers and low molecular weight polymers may also be used herein. The oligomers may be polypropylenes, polybutylenes, hydrogenated isoprenes, hydrogenated butadienes, or the like having a weight average molecular weight between about 350 and about 8000.

In an important aspect of the present invention, the elastomeric composition is substantially tackifier free. Tackifiers are well known in the adhesive arts as a component that is added to an adhesive composition so as to increase the adhesive properties (e.g., peel force) thereof. This provides important benefits because, in addition to increasing tack of an adhesive material, a tackifier acts as a plasticizer for any polymers in the composition with a resulting reduction in tensile properties due to the presence of the tackifier. Preferred embodiments of the elastomeric composition have a very low peel force with a standard substrate (304 stainless steel a #2B finish from M$^c$ Master Carr of Cleveland, Ohio) using the method described in copending U.S. Pat. Application Ser. No. 60/557,272, entitled "Letterpress Application of Elastomeric Compositions", filed in the names of Desai, et al. on Mar. 29, 2004 (P&G Case No. 9592P). Suitable elastomeric compositions have a peel force of less than about 3 N/cm, more preferably, less than about 2 N/cm, even more preferably, less than about 1 N/cm, and most preferably, less than about 0.8 N/cm when evaluated using the method described in the aforementioned application.

In one embodiment, a phase change solvent can be incorporated into the elastomeric composition to lower its melt viscosity, rendering the composition processable at a temperature of 175° C. or lower, without substantially compromising the elastic and mechanical properties of the composition. Detailed disclosure of the phase change solvents can be found in U.S. patent application Ser. No. 10/429,432. Alternatively, the elastomeric composition may also comprise low molecular weight elastomers and/or elastomeric precursors of the above thermoplastic elastomers, and optionally crosslinkers, or combinations thereof. The weight average molecular weight of the low molecular weight elastomers or elastomeric precursors is between about 45,000 and about 150,000.

Suitable elastomeric compositions for use herein are elastic without further treatment and they do not include any volatile solvents whose boiling point is below 150° C.

In certain embodiments the elastomeric composition may include precursor components that are activated by a post treatment step after the elastomeric composition has been deposited onto the substrate, so as to improve or enhance its elasticity and other properties including strength, modulus, and the like. For example, the thermoplastic elastomers described in copending U.S. patent application Ser. No. 10/610,605, filed in the name of Ashraf, et al. on Jul. 1, 2003 that comprise an elastomeric block copolymer having least one hard block and at least one soft block, a macro photoinitiator, a processing oil, and optionally, a thermoplastic polymer and/or a crosslinking agent contain such precursor components. Typically, post-treatments include drying, crosslinking, curing or polymerizing via chemical, thermal, radiation means (e.g., ultraviolet radiation or electron beam radiation), and combinations thereof.

In certain preferred embodiments, a stretch zone or an array of stretch zones may comprise more than one elastomeric composition. In such embodiments the first composition will have at least one of: a greater elastic resistance than any of the other elastomeric composition disposed onto the stretch zone or array of stretch zones, a reduced set when compared to any of the other of the elastomeric compositions disposed onto the stretch zone or array of stretch zones and a reduced stress relaxation. Alternatively, certain portions of an array of stretch zones may comprise a first elastomeric composition and other portions may comprise one or more different compositions.

The substrate provides a continuous medium for deposition of the elastomeric composition and contributes at least a portion of the ultimate strength of a stretch zone. A continuous medium is important, for example for embodiments where the embodiment comprises an array having spaced apart stretch zones. In certain embodiments (e.g., as provided by a fibrous substrate), the substrate can further provide a soft, cloth-like feel to the skin for better wearer comfort. Suitable substrate materials include but are not limited to: films, apertured films, foams, knitted fabric, woven fibrous webs or nonwoven fibrous webs as are known in the art. In some embodiments, the substrates are extensible nonwoven webs made of polyolefin fibers or filaments, such as polyethylene, or polypropylene. The substrate material may be elastic or inelastic, extensible or inextensible, stretchable or non-stretchable. Preferred substrates have a 3-dimensional morphology (i.e., via spacing between fibers, projections, holes, etc.) that facilitates the penetration of the thermoplastic elastomer into the substrate as described below.

Suitable elastomeric compositions are preferably applied to the substrate in a fluid or fluid-like state capable of effecting at least partial penetration into the substrate Such partial penetration must be sufficient so as to provide attachment between the resulting elastomeric composition and the substrate such that the composite remains intact through subsequent process steps, shipment and the article wear cycle. Preferably, the elastomeric composition penetrates only enough to provide the desired integrity during subsequent processing and use of the article. For example, if the substrate is a fibrous substrate, it is believed that elastomeric composition penetration to a depth of about one or two fiber diameters is sufficient to provide such integrity. Means to accomplish sufficient penetration of the substrate of the thermoplastic elastomer upon deposition onto the substrate includes, among other mechanisms, absorption of the elastomer into the substrate matrix, penetration through all or a portion of the thickness of the substrate, engulfing or entrapment of 3-dimensional protrusions from the substrate (i.e., entanglement between the substrate and the composition), penetration of holes in the substrate, wetting of a 3-dimensional surface of the substrate, and the like.

To facilitate such partial penetration, the elastomeric composition suitably has a melt viscosity from about 1 to about 1000 Pa·s at 175° C., 5% strain and a shear rate of 1 s$^1$ according to the method disclosed in published US Pat. Application No. 2003/0091807A1. Preferably, the melt viscosity is between about 5 and about 500 Pa·s, and more preferably from about 10 to about 400 Pa·s. Such elastomeric compositions are suitable for use in application processes that operate at a lower viscosity and/or lower temperature than are typical melt extrusion and/or fiber spinning processes.

The elastomeric composition may be applied to a stretch zone to achieve a total add-on level of from about 5 to about 200 g/m$^2$, preferably from about 20 to about 150 g/m$^2$, and more preferably from about 50 to about 100 g/m$^2$.

An array of stretch zones may have open areas not covered by the elastomeric composition ranging from about 5% to about 90% of the total surface area of the region, preferably from about 10% to about 60%, and more preferably from about 20% to about 40%. As will be recognized, the required open area depends on the specifics or the region or feature where the array is disposed. The selective deposition of elastomeric compositions preferably uses less of the materials than would otherwise be required by the conventional lamination technology using films or sheets. The fibrous substrate in combination with the selective deposition of the elastomeric composition can provide the resulting composite with lower basis weight and higher breathability than a laminate containing a fibrous web layer and a film or sheet layer.

As will be recognized, the stretch zones described herein may also be used in combination with stretch features described in the art (Such stretch features include, but are not limited to an elasticized waist, an elasticized belt, an ear, a side panel, a leg cuff, or a fastener component. See below for a discussion of such features in the section-Diaper Component Description Applicable to All Embodiments of Present Invention). As will be recognized, combining the stretch zones of the present invention with stretch features from the art may provide benefits that neither approach could provide by itself. For example, an elastomeric film could be used to provide a first level of elastic resistance to a stretch feature formed using an elastomeric, breathable three dimensional composite material as described in U.S. Pat. No. 6,303,208 and portions of the stretch feature could further comprise stretch zones of the present invention to enhance the elastic resistance in predefined positions on the stretch feature. Similar structures can also be made by replacing the elastomeric film with one or more elastomeric strands or fibers and providing stretch zones according to the present invention thereto.

Figure 2:
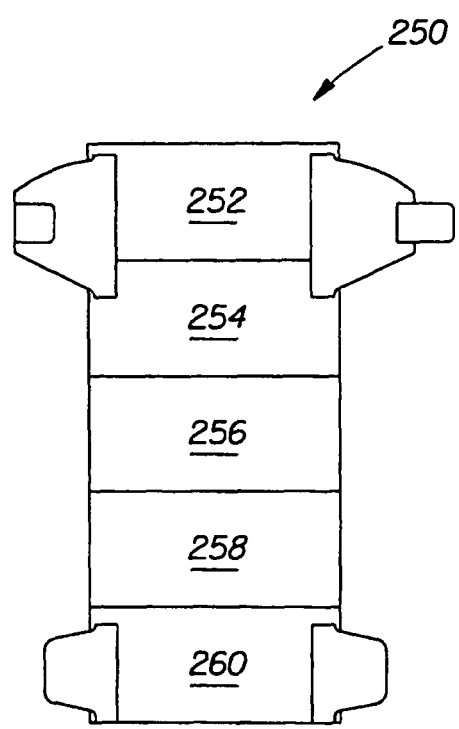
FIG. 2 is a perspective view showing a diaper chassis having a plurality of regions with one or more stretch zones or arrays according to the invention disposed thereon.
Figure 3:
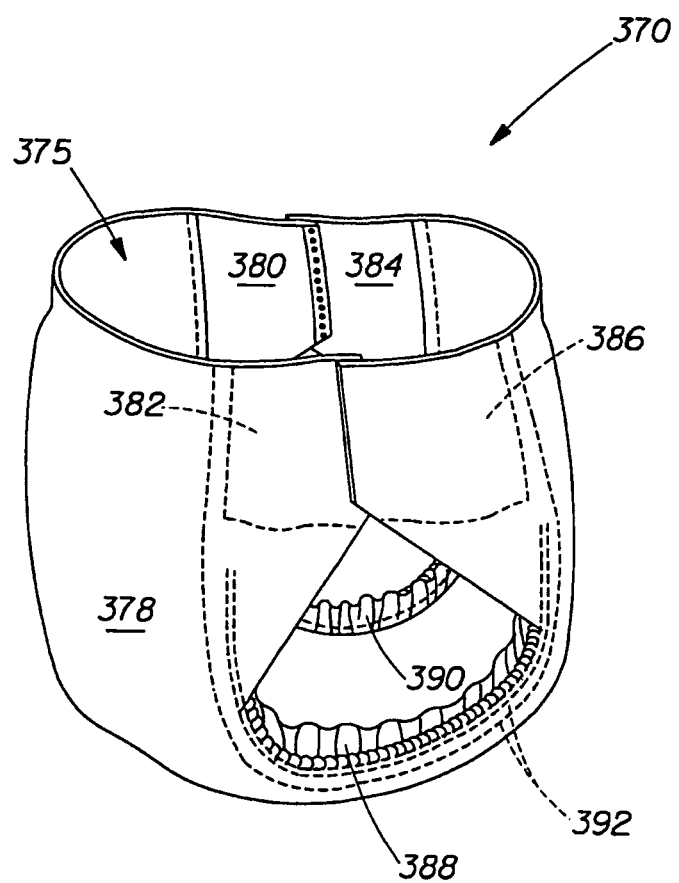
FIG. 3 is a perspective view of a pull-on diaper in accordance with the invention.

Referring to FIG. 1, an absorbent article in the form of an open-style or taped diaper 10 is depicted. It should be understood that while FIGS. 1-3 depict a diaper, the present invention also contemplates other wearable absorbent articles, such as catamenial and adult incontinence products, that encircle or enclose at least a portion of a wearer's anatomy or which are otherwise secured to a wearer. The diaper 10 has a longitudinal centerline 12 and a lateral centerline 14 as a frame of reference for this discussion. The diaper 10 may have a pair of opposed end edges 16 and 18, a pair of opposed side edges 20 and 22, a rear waist region 24, a front waist region 26, a crotch region 28 disposed intermediate the front and rear waist regions 26 and 24, respectively, and a pair of leg regions 30 and 32. The exact size of these various regions vary according to the size of the diaper 10, but generally speaking, the crotch region 28, front waist region 26 and rear waist region 24 represent equal one-third portions along the longitudinal centerline 12. The leg regions 30 and 32 generally represent the one-quarter areas across the width of the diaper 10 in the crotch region 28, and the crotch region 28 itself, represents the remaining center two-quarters or one-half the width of diaper 10.

The diaper 10 also may comprise one or more ears or side panels 34, 36, 38 and 40 disposed generally laterally outboard of the side edges 20, 22 in the front waist region 26 and/or rear waist region 24. In closable diaper 10 at least one fastener element 42 is disposed on one or more of side panels 34 and 36 and is adapted to be secured to at least a portion of the longitudinally opposing front side panels 38 and 40, or a portion of the outer surface of the front waist region 26 or a component thereof. An accompanying fastener element 44 is shown in a folded back configuration to expose the mechanical fasteners 46, which shown as hooks for a hook-and-loop fastening systems commercially available from 3M or Velcro Industries. The fastener element 44 may be capable of engaging loop material embodied in a landing zone 27 located on the outer surface of the diaper 10.

Any one or more of regions 24, 26, 28, 30, 32, 34, 36, 38, 40, 42 or 44 may comprise a stretch zone or array of stretch zones as may be required to provide the desired elasticity in accordance with the present invention. In this way, the diaper 10 may preferably be configured to adapt to the specific wearer's anatomy upon application and to maintain coordination with the wearer's anatomy during wear (i.e., the fit should remain the same with minimal sagging, achieving sustained fit.). Any region of the diaper 10 may include a stretch zone or array of stretch zones. The front waist region 26 and/or the rear waist region 24 and/or side panel regions 34, 36, 38 and/or 40 preferably include at least one stretch zone of thermoplastic elastomer in order to accommodate a wider range of wearer waist dimensions (i.e., provide a wider fit range) and/or to provide sufficient tension around the waist circumference of the wearer. This provides sufficient normal force to the wearer's skin so as to anchor the diaper 10 with respect to the wearer's anatomy, thereby providing sustained fit.

Each stretch zone may have continuous or discontinuous properties in any direction wherein the varying properties include chemical composition, elasticity, extensibility, maximum elongation, other stress/strain properties, vectors or angles, basis weight, geometry, dimensions, 3-dimensional morphology, visual distinctiveness, and the like. A stretch zone may have continuous properties (e.g., because the elastomeric composition, substrate material, treatment, etc.) has relatively homogeneous properties. Alternatively, stretch zones may have discontinuous properties due to provision of non-homogeneous properties thereto. An array may comprise stretch zones having the same or different properties. Suitable stretch zone arrays include a plurality of straight or curved lines or bands, rectilinear shapes, curvilinear shapes, other regular or irregular geometric shapes, and combinations thereof which will be described in more detail hereinafter. Two stretch zones may be longitudinally separated or adjacent, laterally separated or adjacent, or the stretch zones may be at least partially overlapping in such arrays. Within an array, the individual stretch zones may vary in property, geometry, relative orientation, spacing, or elasticity or extensibility. In certain embodiments, at least a portion of at least one stretch zone may be visually distinct. Stretch zones may be combined with other elastic, extensible, or inextensible materials, such as films, webs, strands, and the like to form laminates.

An exemplary diaper chassis comprising arrays of stretch zones is diaper chassis 250 as is shown in FIG. 2. The diaper chassis 250 may include a liquid impermeable backsheet and an outer cover made of a nonwoven material. Other chassis components may be included but are not depicted for purposes of clearly showing the array of stretch zones of the present invention. In one embodiment, a thermoplastic elastomer may be disposed on a standard liquid impermeable backsheet material in a way which creates different arrays of stretch zones in regions 252, 254, 256, 258 and 260. By way of example, an array in region 252 may comprise a first thermoplastic elastomer composition, while arrays in regions 254, 256, 258 and/or 260 may comprise a different composition or comprise the first composition disposed in a different configuration (thickness, width, pattern, etc.). In certain cases for purposes of enhancing fit on a wearer, the various stretch zone properties are symmetrical in that arrays in regions 252 and 260 have similar properties, arrays in regions 254 and 258 also have similar properties while an array in region 256 has a third type of elastic property. It should be understood, however, that this is not necessary and the individual arrays in regions 252, 254, 256, 258 and 260 may vary individually and widely in terms of elastic properties, size, shape, and composition without deviating from the scope of the invention.

Reference is now made to FIGS. 3, 4 and 5A-B which show a pant 370. The term "pant", as used herein, refers to disposable garments having a waist opening and leg openings designed for infant or adult wearers. A pant may be preformed by any suitable technique including, but not limited to, joining together portions of the article using refastenable and/or non-refastenable bonds (e.g., seam, weld, adhesive, cohesive bond, fastener, etc.). A pant may be preformed anywhere along the circumference of the article (e.g., side fastened, front waist fastened). While the term "pant" is used herein, pants are also commonly referred to as "closed diapers", "prefastened diapers", "pull-on diapers", "training pants" and "diaper-pants". Suitable pants are disclosed in U.S. Pat. No. 5,246,433, U.S. Pat. No. 5,569,234, U.S. Pat. No. 6,120,487, U.S. Pat. No. 6,120,489, U.S. Pat. No. 4,940,464, U.S. Pat. No. 5,092,861, U.S. patent application Ser. No. 10/171,249, entitled "Highly Flexible And Low Deformation Fastening Device", filed on Jun. 13, 2002; U.S. Pat. No. 5,897,545, U.S. Pat. No. 5,957,908.

Figure 4:
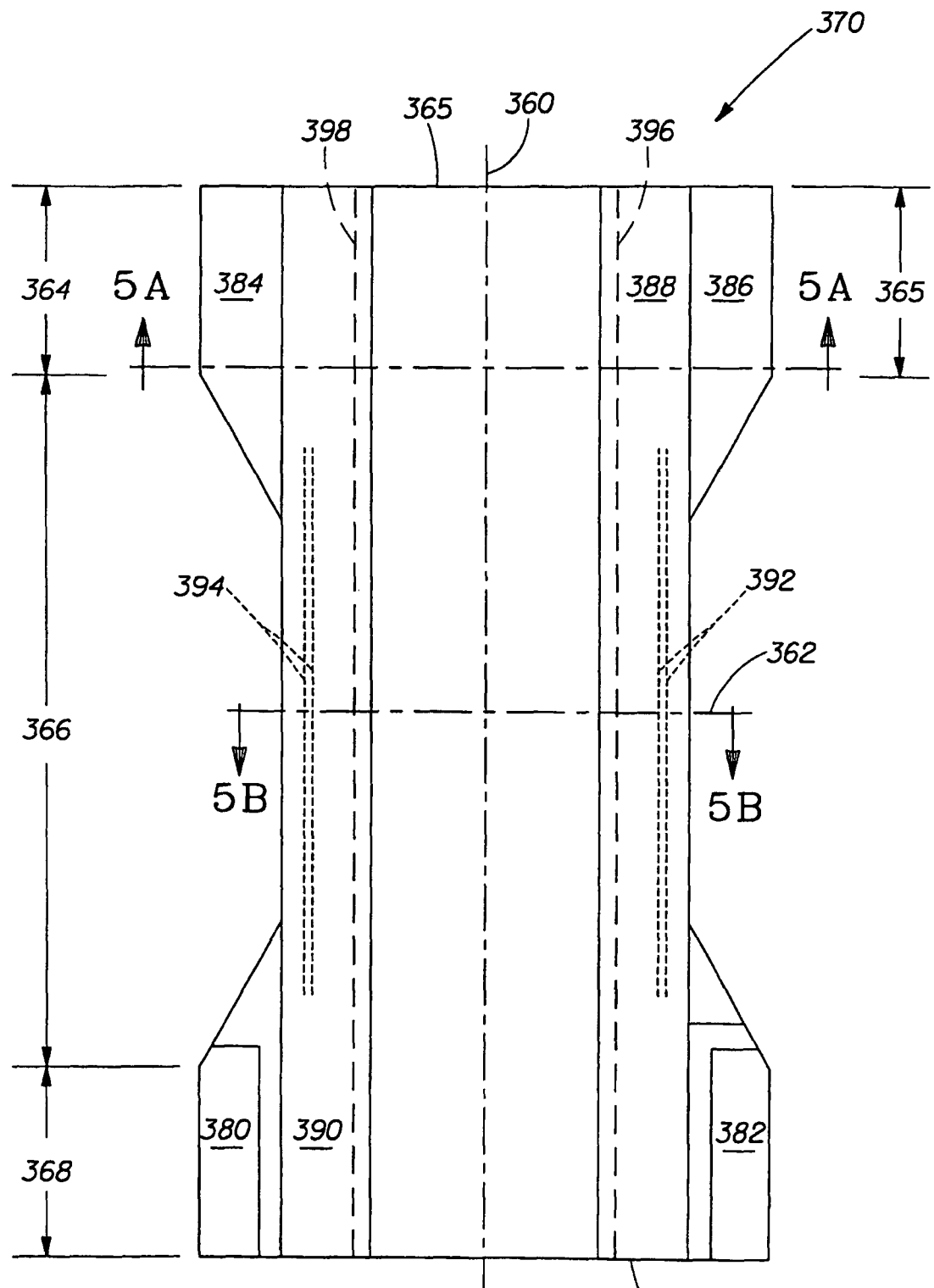
FIG. 4 is a plan view of the pull-on diaper of FIG. 2.
Figure 5A:
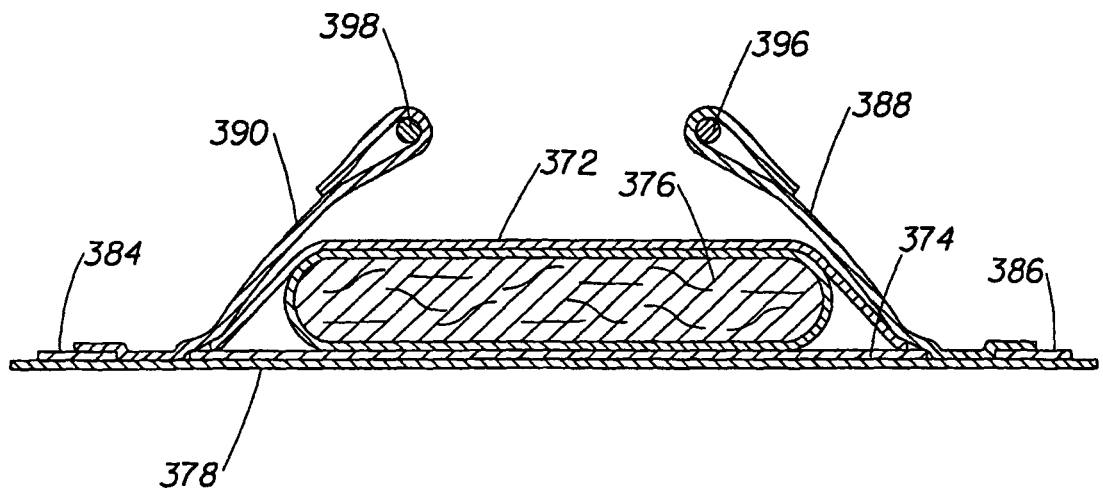
FIGS. 5A and 5B are cross-sectional views of the pull-on diaper shown in FIGS. 3 and 4.
Figure 5B:
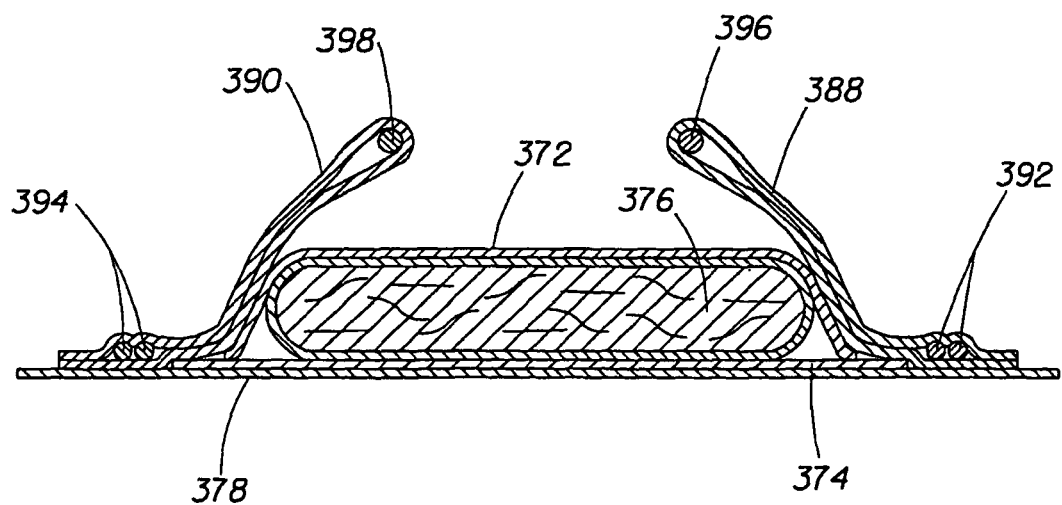

Pant 370 may include stretch zones to impart the desired elastic properties so that it can be donned easily and sustain better fit and comfort. Similar to the diaper 10, stretch zones may be included anywhere on the pant 370. FIG. 3 is a perspective view of pant 370 and FIG. 4 shows pant 370 in a plan view. As shown therein, pant 370 has a longitudinal centerline 360, lateral centerline 362, a front waist region 364 (adjacent front waist edge 365), a crotch region 366 and a rear waist region 368 (adjacent rear waist edge 369). As can be seen most clearly in FIGS. 5A-B, pant 370 may include an absorbent assembly including liquid permeable topsheet 372, a liquid impermeable backsheet 374, and an absorbent core 376 disposed between the topsheet 372 and the backsheet 374. An outer cover 378 (typically comprising a nonwoven) is disposed on the outer surface of the pant 370. Two pair of side panels 380, 382 and 384, 386 are attached to the outer cover 378 in the front waist region 364 and the rear waist region 368, which in turn, is attached to the backsheet 374 of the absorbent assembly so as to form a pair of leg openings and a waist opening for the wearer. Preferably, stretch zones areas are disposed in at least one of the side panels 380, 382, 384 and/or 386. The stretch zones of pant 370 may also comprise the waist regions 364, 366, barrier leg cuffs 388 and 390. For example either or both of the leg elastics 392, 394, and/or the barrier leg cuff elastics 396, 398 could comprise an elastomeric composition where the composition is disposed on a substrate so as to form a stretch zone in one of the features shown in FIGS. 5A and 5B.

Belt structures (not shown) may also comprise the stretch zones of the present invention. One such alternative structure comprises the ear and/or side panel and at least a portion of the waist functionality. In another alternative belt structure, a belt completely encircling a wearer's waist (i.e., a 360 degree belt) may be formed, for example, by depositing one or more laterally oriented stretch zones (or an array thereof) adjacent the front and rear waist edges 365, 369 so as to form a band of tension about the wearer's waist. Such stretch zones could also comprise those shown in FIGS. 7A, 7B and 8A-D.

Reference is made to FIGS. 6A-I in which various side panels 604, 606, 608, 610 are depicted for a closable open or taped diaper 612. As will be recognized, the side panels 604, 606, 608, 610 each have an inner edge 634, 636, 638 and 640 disposed at a predefined angle (usually parallel) with respect to longitudinal centerline 650. It should be understood that the side panels 604, 606, 608 and 610 as described herein are interchangeable with any of the side panels or ears described in FIGS. 1-4 of the diapers 10 or 250 or pant 370 and with any of side panels 605, 607, 609, 611, 613, 615, 617, and 619 of FIGS. 6B-6I. The stretch zone arrows 614, 616 are depicted to show exemplary force vectors desirable of typical side panels in diapers. The size of a given stretch zone in a region of the diaper 612 is dependent on the function of the stretch zone and the desired tension/extension vectors 614, 616 in that given region of the diaper 612. Each stretch zone may be smaller or larger than the region of the diaper 612 in which it is primarily disposed. A given stretch zone may also overlap other regions of the diaper 612.

Figure 6A:
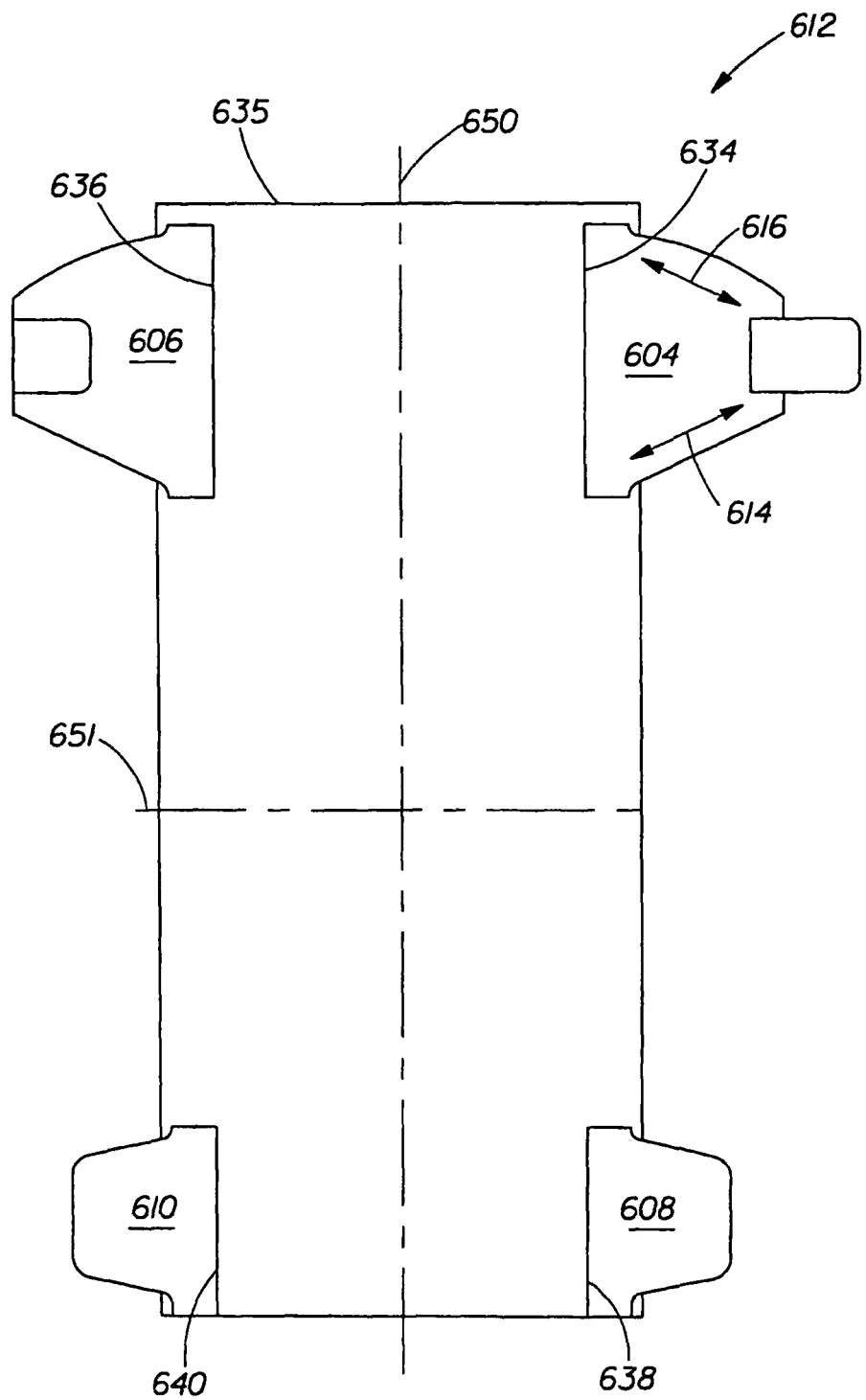
FIGS. 6A-I show a diaper embodiment of the present invention in which the diaper ears have stretch zones in various designs.
Figure 6B:
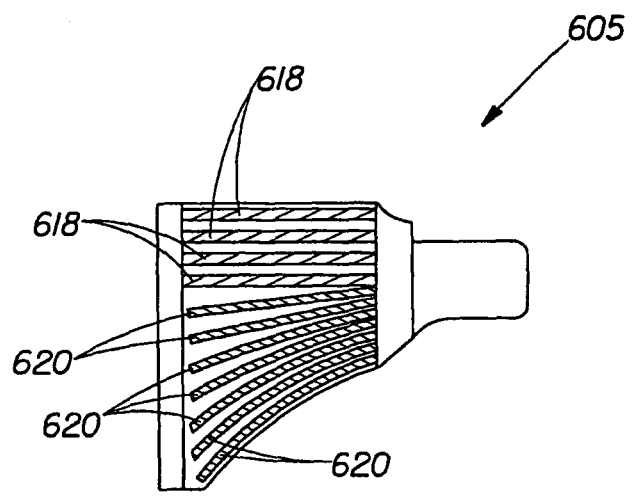
Figure 6C:
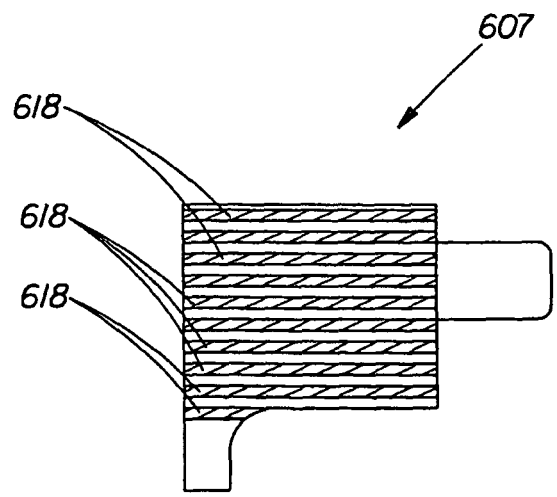
Figure 6D:
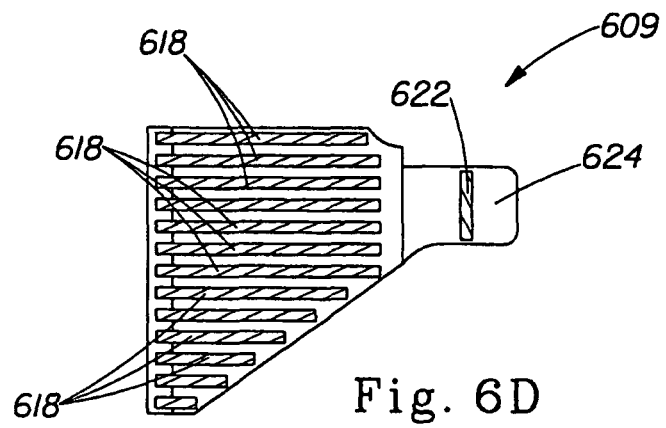
Figure 6E:
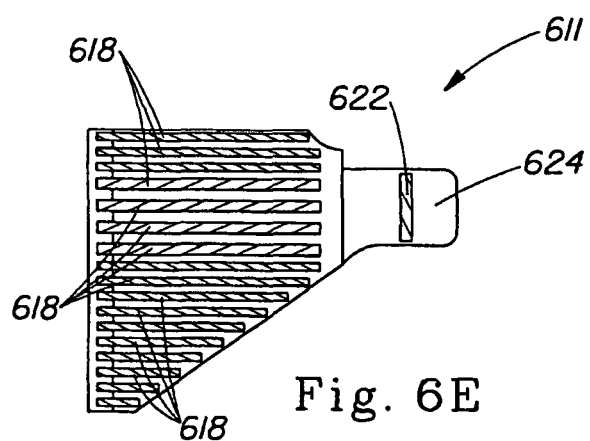
Figure 6F:
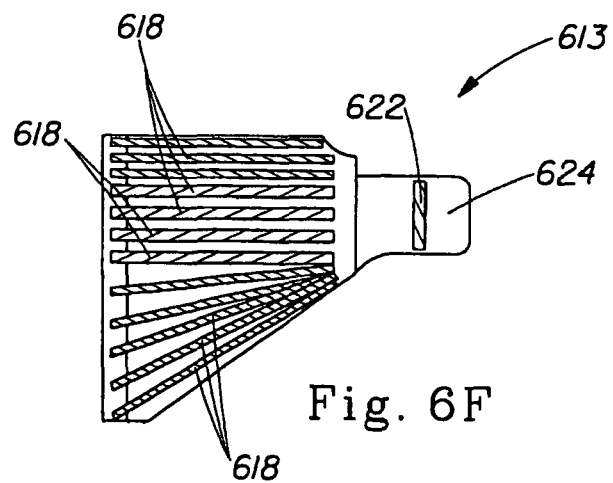

Referring to FIGS. 6B-6I, various linear stretch zones 618 of side panel 605 may be configured as lines or strands generally having widths less than about 2 mm and typically less than about 1 mm. Linear stretch zones 618 may also be configured as bands generally having widths between about 2 mm and about 40 mm and aspect ratios ranging from about 2:1 to about 100:1. Linear stretch zones 618 may also be disposed at an angle with respect to the lateral centerline 651 (FIGS. 6B and 6F). Preferred angles are in the range 0±70°. Stretch zones having a predominately lateral orientation are generally wider and have a higher modulus than those having a generally longitudinal orientation. Curved stretch zones 620 may be either concave or convex with respect to the longitudinal or lateral centerlines 650, 651, or both and may have radii of curvature greater than about 1 mm, preferably greater than about 10 mm, more preferably greater than about 50 mm. The curvature may optionally be variable over the length or "path" of the stretch zone 620. Typically, the thickness of stretch zones 618 and/or 620 may be in the range of about 0.02 mm to about 5 mm and the basis weight is in the range of about 20 g/m² to about 300 g/m².

Figure 6G:
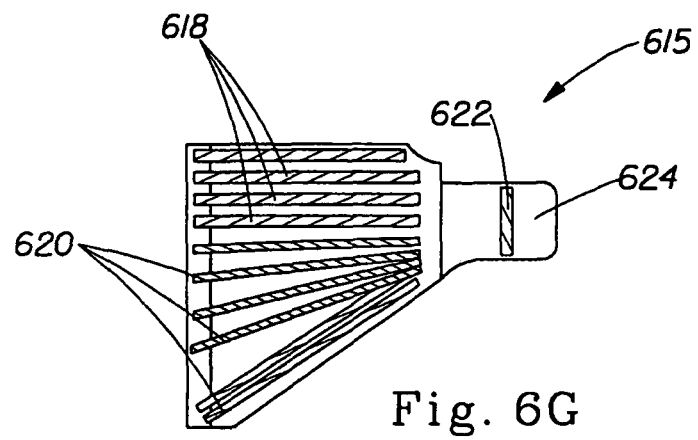
Figure 6H:
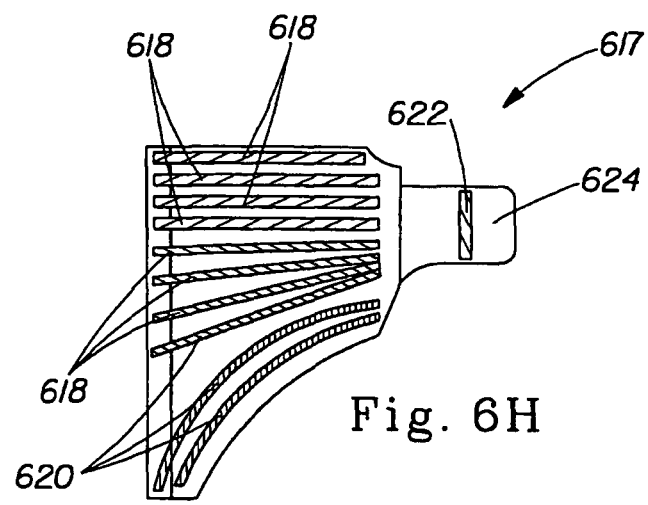
Figure 6I:
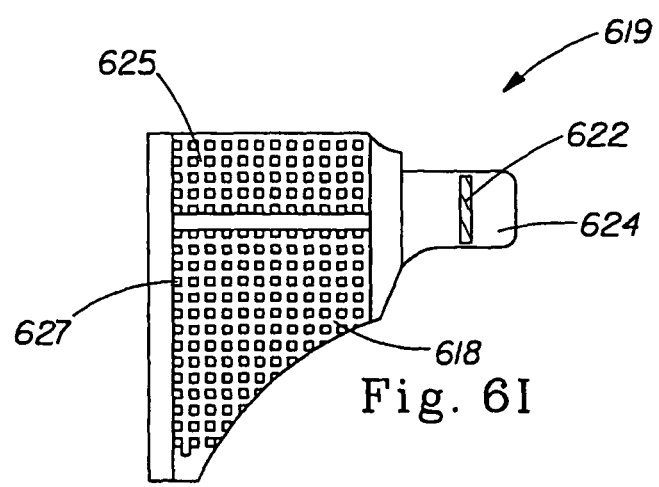

Additional exemplary embodiments of the invention are shown in FIG. 6C with side panel 607, FIG. 6D with side panel 609, FIG. 6E with side panel 611, FIG. 6F with side panel 613, FIG. 6G with side panel 615, FIG. 6H with side panel 617, and FIG. 6I with side panel 619. All of the side panels 609, 611, 613, 615, 617, 619 may be integral with or separately attached to the diaper chassis of the diaper 10 or pant 370 described previously. Also all of the stretch zones 618 and 620 comprise an elastomeric composition as described herein. FIGS. 6D-6I show additional stretch zones 622 applied to or formed as part of the fastener element 624 to impart other desired elastic properties of the present invention.

Alternatively, one or more, but not all, of stretch zones 618, 620 may comprise an elastomeric composition that differs from the composition used to form the remainder of the stretch zones 618, 620. For example, referring to FIGS. 6B and 6C, certain stretch zones 618 that lie longitudinally outboard (i.e., closer to rear waist end 635) of the remainder of stretch zones 618 may comprise an elastomeric composition with a higher elastic modulus so as to provide a larger elastic resistance around the circumference of a wearer's waist. Alternatively (FIG. 6B), stretch zones 618 may comprise a first elastomeric composition and stretch zones 620 may comprise a second elastomeric composition. Again, stretch zones 618 lie longitudinally outboard of stretch zones 620.

Alternatively, an array of linear stretch zones 618 or curved stretch zones 620 or both may comprise a spiral or an overlapping or entangled configuration, for example a cross hatch array. Suitable stretch zone shapes (not shown) include rectangles, circles, ellipses, diamonds, triangles, parallelograms, trapezoids, wedges or other sections of circles or ellipses, other polygons, or other irregular enclosed shapes.

One particularly preferred embodiment of an array of stretch zones is shown in FIG. 6I where side panel 619 comprises a pair of cross hatch arrays 625, 627. As shown therein, both of arrays 625, 627 comprise a plurality of linear stretch zones 618 in an overlapping, cross hatch pattern where the individual stretch zones 618 have either a predominately lateral orientation or a predominately longitudinal orientation. As will be recognized and described herein, the stretch zones 618 can also be at an angle other than 0° or 90° with respect to the centerlines.

In one embodiment of side panel 619 shown in FIG. 6I, array 625 has different mechanical properties than array 627. In particular, first array 625 has a lower available strain than second array 625. As used herein, "available strain" is the strain at which there is an abrupt increase in elastic resistive force in response to an applied elongation. Such change typically occurs when the applied elongation has reached the point where a meaningful portion of the resistive force is provided to a stretch zone by the substrate. At applied elongations less than the available strain the elastic resistive force is substantially provided to the stretch zone by the elastomeric composition. This difference in available strain is because array 627 must be able to stretch to a greater extent in order to conform to the full range of movement of a wearer's legs. Similarly, first array 625 has different elastic resistance than second array 627. Suitably, array 625 has an elastic resistance at 25% strain of between about 0.05 N/cm and about 50 N/cm, preferably between about 0.1N/cm and about 40 N/cm, more preferably between about 1 N/cm and about 30 N/cm. The ratio of elastic resistance at 25% elongation of array 625 to the elastic resistance at 25% elongation of array 627 is suitably greater than about 1.25:1, preferably greater than about 1.5:1, more preferably between about 2.0:1 and about 6.0:1. The difference between available strains of arrays 625 and 627 is suitably at least about 25% (i.e., if array 625 has an available strain of about 25%, then the available strain of array 627 would be at least about 50%), preferably the difference is at least about 50%.

Figure 7A:
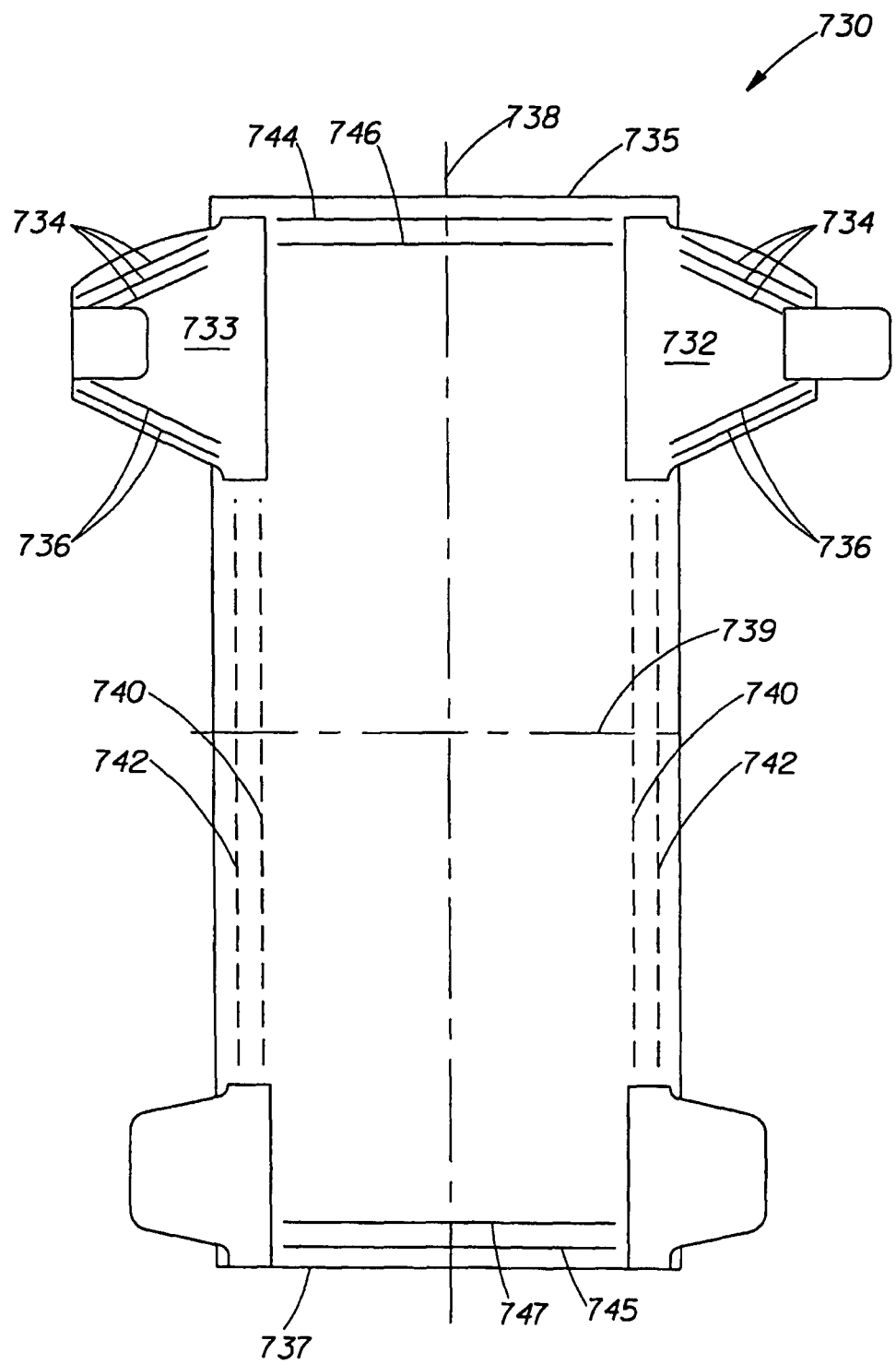
FIGS. 7A and 7B show yet another embodiment of a diaper in accordance with invention wherein stretch zones are provided to the ears and along the absorbent assembly for imparting the desired elastic properties to the diaper.
Figure 7B:
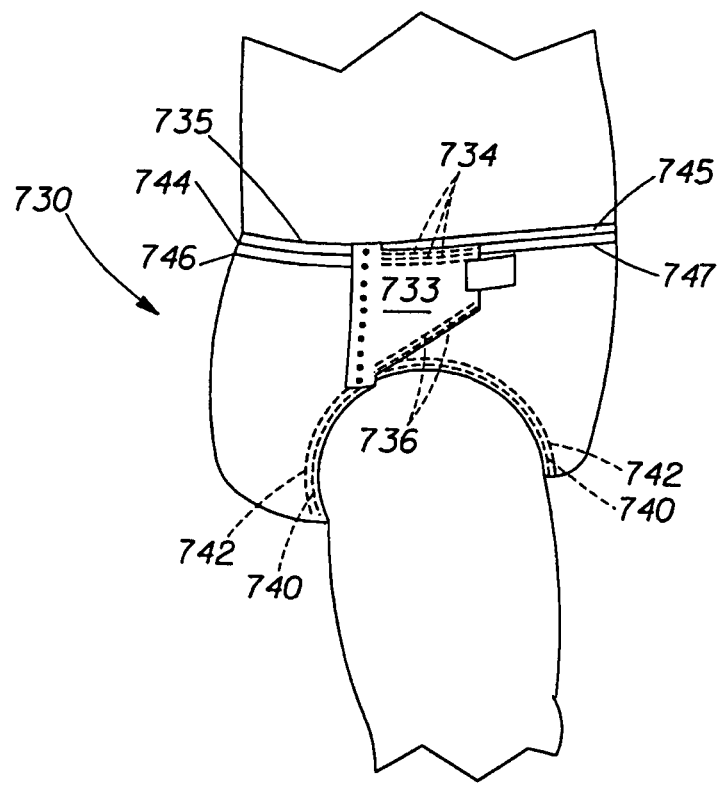

Referring to FIGS. 7A and 7B, a diaper 730, similar to diaper 10 and having a longitudinal centerline 738, a lateral centerline 739, a rear waist end 735 and a front waist end 737, is depicted in which the waist and thigh portions of the side panel 732, 733 preferably comprise different stretch zones 734 and 736, varying in tension and/or angle as shown. Preferably, the side panel stretch zone 734 nearer the rear waist end 735 of diaper 730 may be oriented at an angle of about 0 to about minus 50 degrees from the lateral centerline 739, more preferably between about −5 degrees and about −40 degrees from the lateral centerline 739. Preferably, the stretch zone 736 may be oriented at an angle of about 0 to about plus 70 degrees from the lateral centerline 739, more preferably between about +20 degrees and about +60 degrees from the lateral centerline 739. One preferred side panel 732 stretch zone embodiment includes a stretch zone 734 oriented at about −10 to −20° from the lateral centerline 739 and a stretch zone 736 oriented at about +20° to +50° from the lateral centerline 739.

In certain preferred embodiments, at least one of the side panel stretch zones 736 may be aligned with the end of the outer leg cuff elastics 740, 742 in order to provide an effective extension of the leg cuff elastic, thereby encircling a wearer's leg with a combination of stretch zone 736 and 740, 742 shown in FIG. 7B. That is, the outer leg cuff elastics 740, 742 and the side panel stretch zones cooperate to provide a substantially continuous line of force to encircle a wearer's legs.

In other preferred embodiments, at least one of the waist regions adjacent rear waist end 735 or front waist end 737 is also provided with one or more waist stretch zones 744, 745, 746, 747. In such embodiments the waist stretch zones 744, 745, 746, 747 may be aligned with the ear stretch zones 734 that are disposed adjacent to the rear waist end 735 so as to provide a substantially continuous line of force encircling a wearer's waist. Depending on the design of diaper 730, such a line of force may follow the low motion zone of a wearer (see below) or be juxtaposed with another portion of a wearer's anatomy while encircling the waist.

Regardless of the specific construction, composition, or geometry, or stretch properties of the side panel 732, the stretch zones 734 and 736 in the waist and thigh portions are preferably capable of substantially independent action with respect to one another. Certain embodiments may include an additional side panel stretch zone (not shown) functioning as a transition between the leg and thigh portions, i.e., a "transition zone". The transition zone may have distinctly different stretch properties (or even not be elastic at all) than either the leg or waist zones and functions to decouple or separate the deformations caused by the leg and waist panels, allowing them to act independently without interaction with each other. In embodiments comprising a side panel transition zone, the transition zone may be substantially extensible to further promote independent action between the waist and thigh zones of the side panel, while still providing sufficient stretch to accommodate the relative movements of the waist and thigh zones while being worn by a wearer, helping to control buckling and/or folding of the transition region.

Figure 8A:
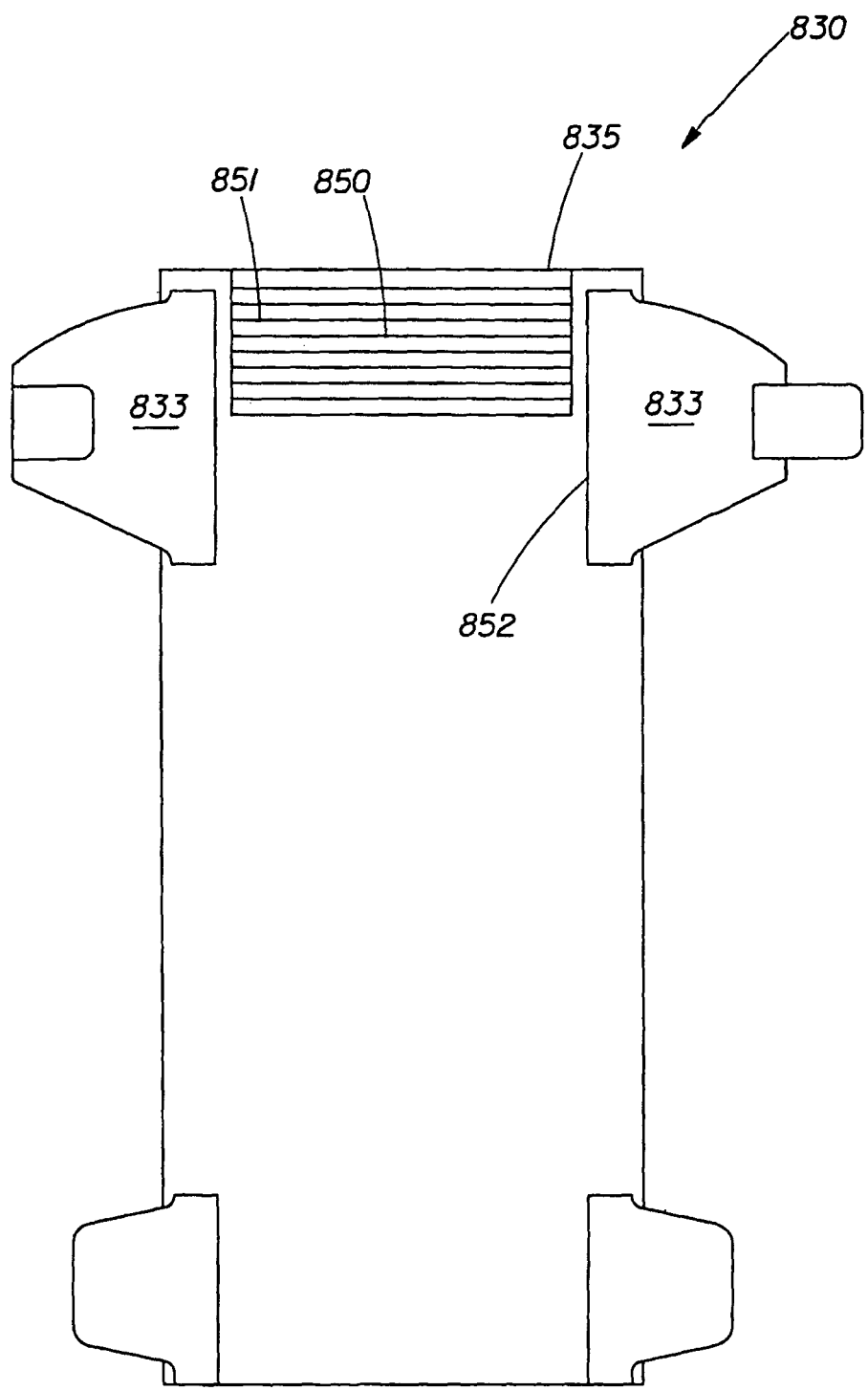
FIGS. 8A-D illustrate a diaper in which stretch zones are disposed in a variety of locations to provide several alternative designs for improved wearer comfort and fit.
Figure 8B:
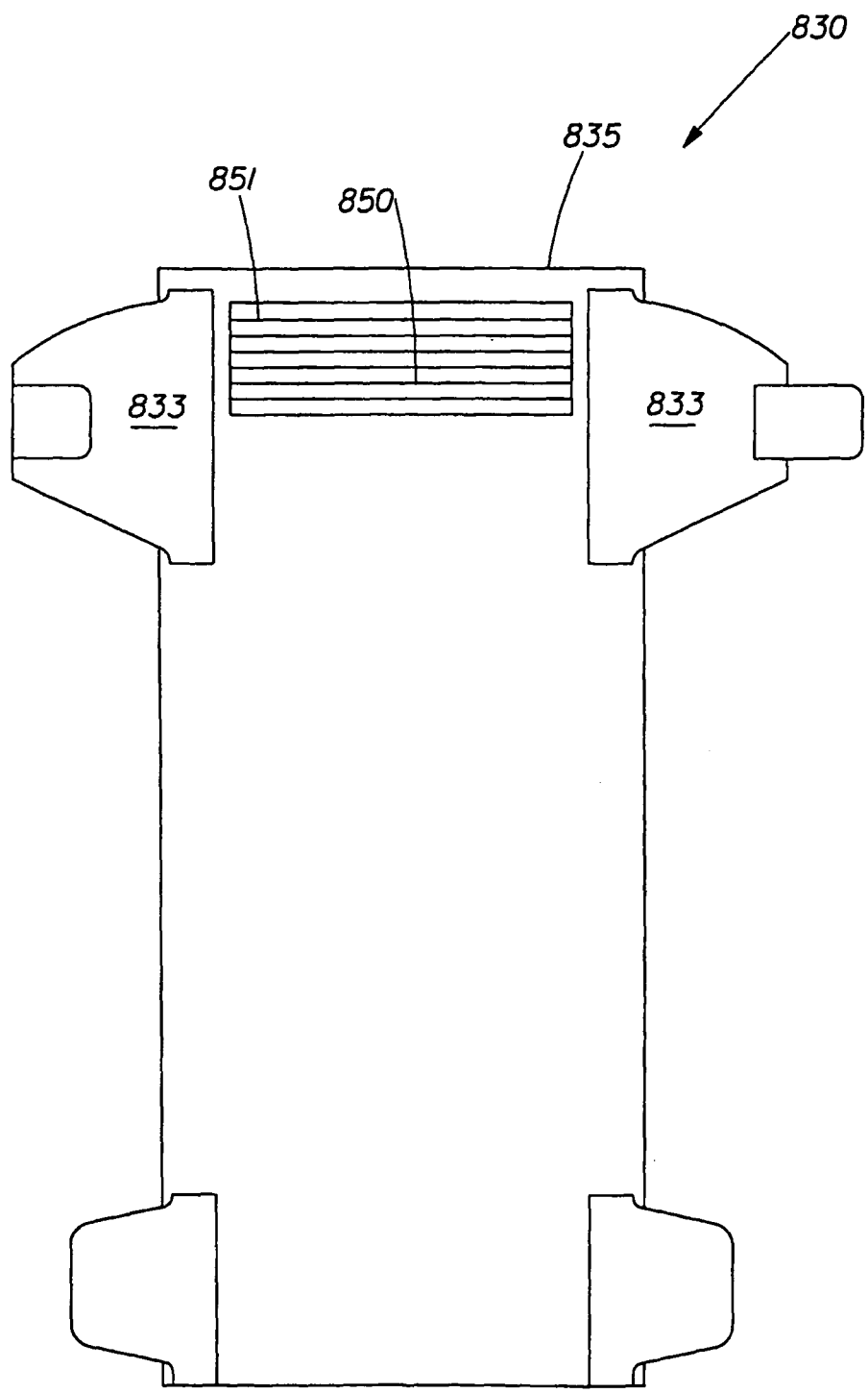
Figure 8C:
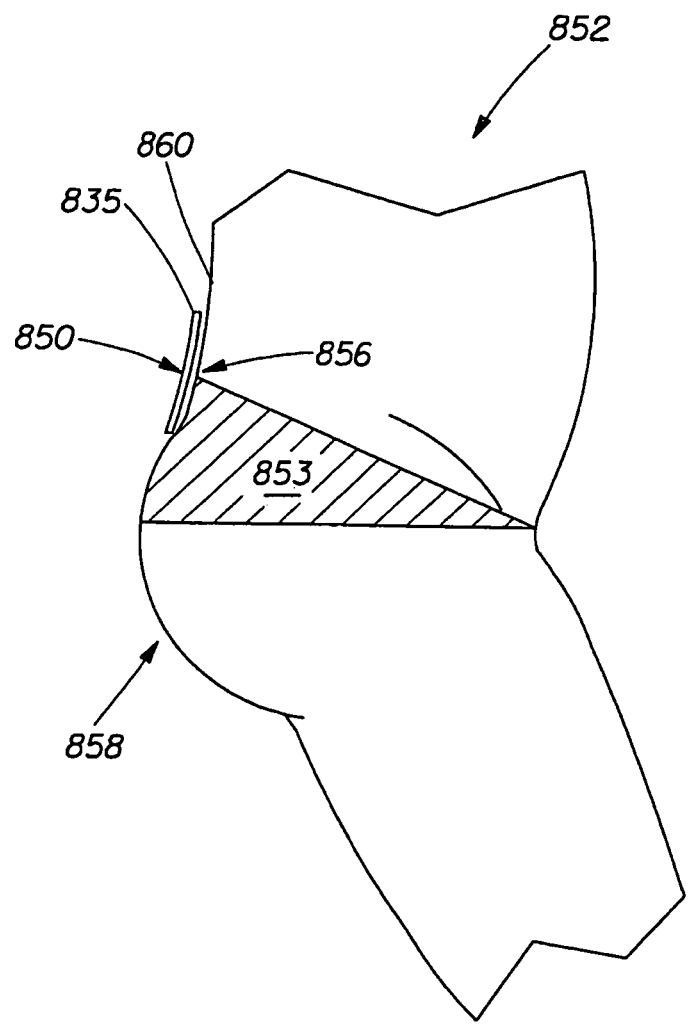

Referring to FIGS. 8A-D, at least one array 850 of stretch zones 851 may be included in the waist region of the diaper 830. The array 850 of stretch zones 851 may have similar or varying degrees of elasticity or extensibility and may assume any geometry or orientation. For example, in FIG. 8A the array 850 of stretch zones 851 is located at the waist end 835 of diaper 830, whereas FIG. 8B shows another embodiment in which the array 850 is offset from waist end 835. It may be preferable to have array 850 located generally in the lower back waist area as shown on a partial side view of wearer 852 in FIG. 8C. In this way, the maximum fit and comfort will be experienced by the wearer 852 as the tension is applied by the article to the wearer's body at or immediately above the convexity of the buttocks (i.e., the "buttocks shelf"), contributing to the overall anchoring capability of the article (i.e., its ability to resist sagging). Said another way, the array 850 and stretch zones 862, 864, 866, 868 and 870 (shown in FIG. 8D) co-operate to maintain diaper 830 in an optimal fit configuration with respect to the low motion zone 853 (i.e., the line or zone connecting the lumbar curve of the back over the hips to under the abdominal crease of a wearer's body 852) so as to maximize the performance thereof. For a more detailed discussion of low motion zones see U.S. Pat. No. 5,358,500.

Figure 8D:
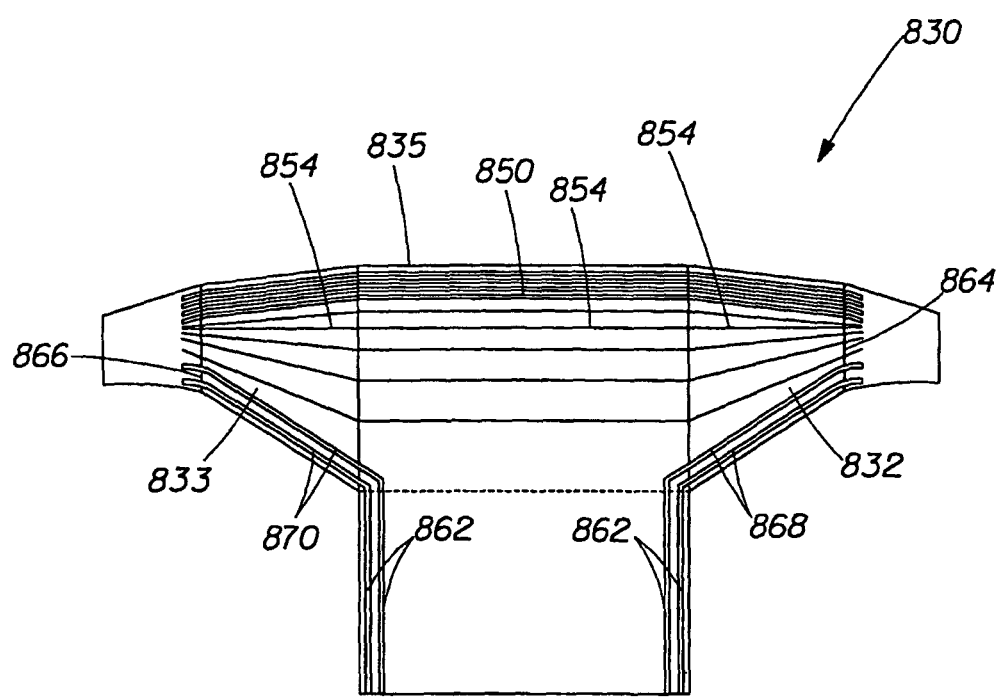

In certain preferred embodiments as shown in the partial plan view of diaper 830 in FIG. 8D, array 850 comprises one or more stretch zones 854 having higher localized elastic resistances (i.e., a "high tension" stretch zone 854) aligned with the waist end 835. The high-tension stretch zones 854 may be adjacent the waist end 835 or may be disposed inboard thereof. Typically, the high-tension stretch zones 854 are disposed between about zero and 30 mm from the waist end 835 of the diaper 830. Preferably, the high-tension stretch zones 854 are disposed less than about 20 mm from the waist end 835. Generally, an array 850 of the high-tension stretch zones 854 may correspond to an area 856 on the wearer 852 body immediately above or at the upper curvature of the buttocks 858 where the high-tension stretch zone 854 functions to provide additional anchoring capability for the diaper 830 by applying a normal force to the geometric "shelf" created by the buttocks 858. The high tension stretch zones 854 additionally hold the waist end 835 of the diaper 830 against the wearer's back 860 preventing back waist gapping.

In embodiments comprising an array 850 of stretch zones 854 at or near the waist end 835 of diaper 830 and extending through multiple regions of the back waist and crotch of the article, the remaining area of the waist end 835 may have either a lower elastic resistance, may be primarily extensible, or may comprise areas with either property. In any case, this waist end 835 area (i.e., the area not including the stretch zones 850 or 854) may be a low-tension zone.

Referring again to FIG. 8D, stretch zones 862 may be substantially parallel to the proximal edges 864 and 866 of side panels 832 and 833, respectively. Optionally, transition stretch zones 868 and 870 may be disposed intermediate stretch zones 854 and 868, 870. The stretch zone 854 may provide a primary anchoring function and stretch zones 862, 868 and 870 may provide a dynamic leg motion accommodation function. While stretch zones 854, 868 and 870 all provide an elastic resistance, the present invention allows tailoring such forces in both to degree and direction to meet the different needs of the anchoring and motion accommodation functions. Referring again to FIG. 8C, preferably, the region covering a wearer's buttocks 858 comprises at least one extensible stretch zone so as to provide adequate coverage thereof, conform to the wearer 852 shape, and relieve stress in the transition region between the crotch as and the waist end 835 region of the diaper 830 (FIGS. 8 A, B and D) as it goes between the wearer 852 legs. As described previously, side panels 832 and 833 may comprise distinct stretch zones 854, 862, 868 and 870 having different functions and may be single stretch elements having different properties throughout the stretch zone or have physical delineations between stretch zones 854, 862, 868 and 870 such as slits, holes, or other deformation. However, stretch zones 854 and 862 preferably comprise stretch elements, or arrays of stretch elements, having different properties, geometry, and/or dimensions from each other Typically, stretch zones 854 exhibit an elastic resistance of at least about 0.05 N/cm when strained to 25% elongation. Preferably, stretch zone 854 exhibits an elastic resistance of between about 0.05 N/cm and about 50 N/cm when strained to 25% elongation, more preferably between 0.1 N/cm and about 40 N/cm and most preferably between 1 N/cm and about 30 N/cm. Preferably, stretch zones 854 experience less than about 40% force relaxation and less than about 15% set. Typically, stretch zones 854 will have a maximum elongation of at least about 25%, preferably between about 50% and about 300%. Typically, stretch zones 862 exhibit an elastic resistance of at least about 0.05 N/m when strained to 25% elongation. Preferably, the stretch zones 862 exhibits an elastic resistance of between about 0.1 N/cm and about 8 N/cm when strained to 25% elongation. Preferably, stretch zones 862 experience less than about 40% force relaxation and less than about 15% set. Typically, stretch zones 862 may have a maximum elongation of at least about 25%, preferably between about 50% and about 200%. Additionally, stretch zones 868 and 870 may exhibit a lower resistive force upon elongation than either stretch zones 854 and 862 at a given extension. Typically, the ratio of elastic resistance of stretch zone 854 to stretch zone 868 or 870 is at least 1.25:1, preferably at least 1.5:1, and most preferably between about 2.0:1 and 6.0:1. Regardless of the stretch properties of the individual stretch zones 854, 862, 68 and 870, the overall tension of the side panels 832 and 833 region when extended to 25% is preferably less than 20 N, and the force relaxation is less than 40%.

Figure 9:
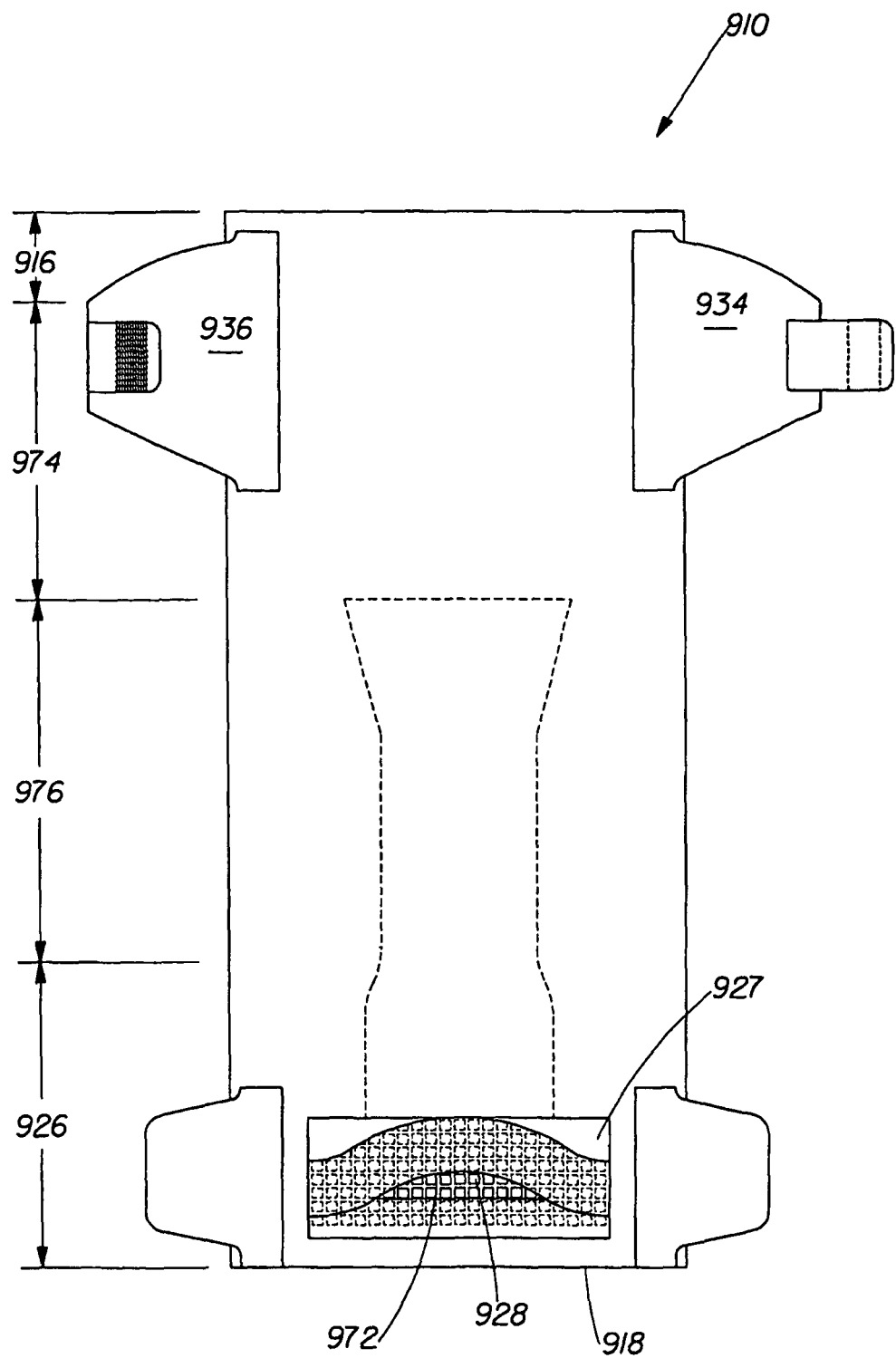
FIG. 9 is a plan view of a diaper in accordance with the invention in which stretch zones are provided in the diaper ears and the front waist portion.

Referring to FIG. 9, showing diaper 910 is depicted in which the front waist region 926 may comprise at least one stretch zone 972 The function of stretch zone 972 is to dynamically accommodate the contraction and expansion cycles of the wearer's abdomen as the wearer moves and/or changes position, preventing front waist sagging. Stretch zone 972 is preferably substantially aligned with the front waist end 918 of the diaper 910. In closable versions of diaper 910 including a fastening landing zone 927 disposed in or near the front waist end 918, the landing zone 927 may be shaped in a configuration presenting a concavity 928 to the front waist end 918 of the diaper 910. In these embodiments, stretch zone 972 may at extend into the landing zone concavity 928, as shown in FIG. 9.

While the buttocks region 974 located in the back waist region in proximity to the crotch region 976 as shown on diaper 910 may comprise either elastic or extensible portions, or a combination thereof, in preferred embodiments, the buttocks region 974 may be provided with a pattern of thermoplastic elastomer so as to provide a low level of elastic resistance to a stretch zone therein causing the buttocks region 974 to better conform to a wearer's anatomy so as to accommodate the largest wearer circumference (i.e., the buttocks), including the volume of the absorbent core 950, allowing the buttocks region 974 to have a lower on-wearer tension than the rear waist end 916 region. The buttocks region 974 may have stretch zones with extensibility that allows for a smoother geometric transition from the constricted crotch region 976 between the wearer's legs to the side panels 934 and 936 which may have stretch zones similar to those described in FIG. 9D for anchoring. The buttocks region 974 preferably may elongate further than the waist end 916 region to accommodate the wearer's anatomic shape.

Figure 10:
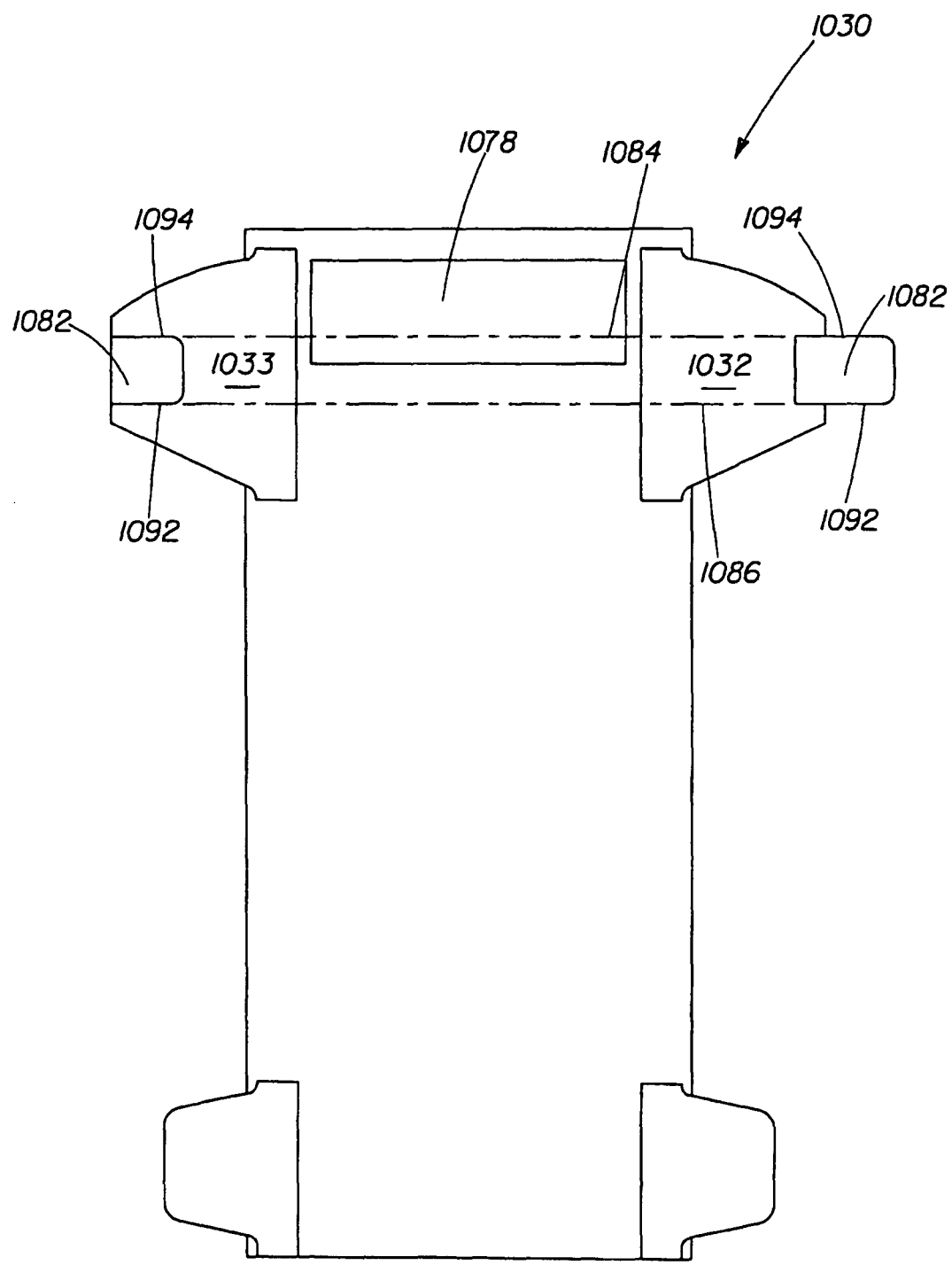
FIG. 10 is a plan view of a diaper in accordance with the invention in which the stretch zones are provided in the rear waist portion such that there is at least partial longitudinal alignment with the diaper ears.

Referring to FIG. 10, another embodiment, diaper 1030, is shown in which a stretch zone 1078 in the waist region may be preferably aligned with the side panels 1032 and 1033 and/or the fasteners 1080 and 1082 disposed on side panels 1032 and 1033 in order to create a substantially continuous line of tension around the waist to promote conforming sustained fit. As shown in FIG. 10, the stretch zone 1078 preferably at least partially overlaps one of the two imaginary lines 1084 and 1086 that connect the longitudinally outboard edges 1092, 1094 of fasteners 1082.

Figure 11:
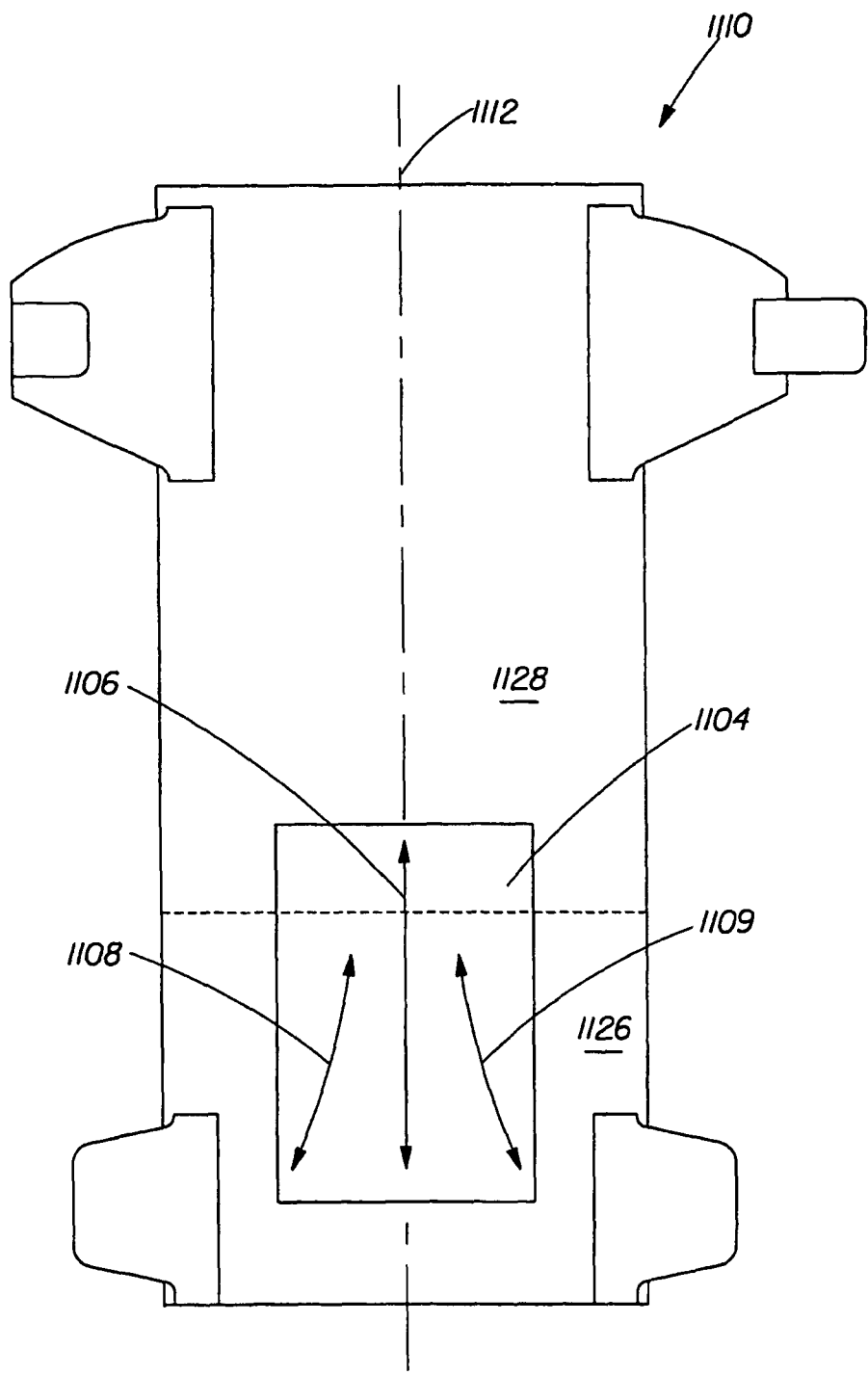
FIG. 11 is a plan view of a diaper having stretch zones in the front crotch portion in accordance with the invention.

Referring to FIG. 11, an array 1104 of stretch zones is shown on diaper 1110 in the front crotch region 1128 spanning into the front waist region 1126. The stretch zones comprising array 1104 may be primarily parallel to longitudinal centerline 1112 of the diaper 1110 allowing better fit in the front crotch region 1128 by providing an elastic resistance along the centerline 1112 as depicted by arrow 1106. Array 1104 should only have a low elastic resistance so as not to pull the front of diaper 1110 down, resulting in sagging. Also, array 1104 should have low available strain so that it hits a force wall after straining a small amount in the machine direction for improved coverage in the front waist area. Typically, array 1104 provides an elastic resistance at 25% strain of between about 0.005 N/cm and about 5 N/cm preferably between about 0.01 N/cm and about 2 N/cm. In certain embodiments the elastic resistance ranges from about 0.1N to about 1 N/cm.

The available strain of the array 1104 in the machine direction is less than about 100%, preferably less than about 50% and more preferably less than about 25%. For the whole diaper, the maximum extension in the machine direction at a load of 5 N is less than about 20 cm, preferably less than about 10 cm, and more preferably less than about 5 cm. Preferably, the area of greatest extensibility is substantially aligned with and overlapping the longitudinal centerline 1112. In another embodiment, array 1104 can be replaced by an individual stretch zone (not shown) providing an equivalent elastic resistance. Preferably, the area of greatest extensibility is substantially aligned with and overlapping the longitudinal centerline 1112. In another embodiment, array 1104 can be replaced by an individual stretch zone (not shown) providing an equivalent elastic resistance. Alternatively, array 1104 may also comprise stretch zones laterally outboard of and at an angle to the longitudinal centerline 1112 and diverging toward the front corners of diaper 1110 as shown by arrows 1108 and 1109 in FIG. 11. These lines or arcs of tension may be primarily elastic so as to provide suitable suspension for the absorbent core and wearers' waist held therein by "connecting" these loads to the anchoring zones of the article via suitable lines, or "paths" of tension. Alternatively, these "load distribution elements" may comprise lines, arcs, bands, or other geometric regions of inextensibility in the surrounding areas of crotch region 1128 and front waist region 1126 and may extend to accommodate the wearer's rise, while the outboard inextensible load distribution elements provide support for a waste load.

Figure 12:
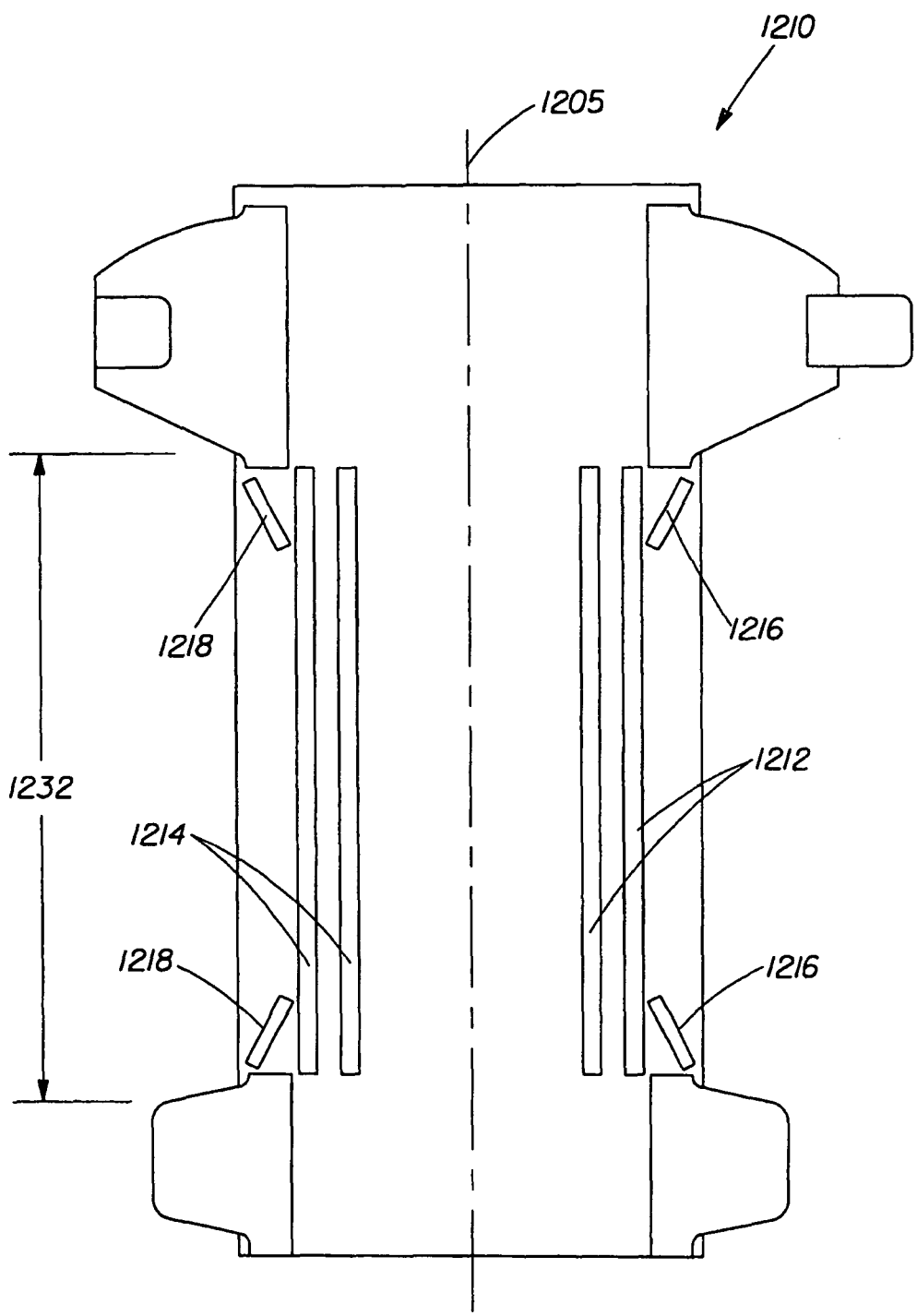
FIG. 12 is another plan view of a diaper in which stretch zones are disposed along the lateral portions of the diaper in order to provide the desired elastic properties in the leg openings.

Referring to FIG. 12, another embodiment, diaper 1210 is shown in which leg regions 1230 may comprise stretch zones 1212 and 1214. Preferably, stretch zones 1212 and 1214 are substantially parallel to longitudinal centerline 1205 and are highly elastic. Alternatively, stretch zones 1212 and 1214 may also be curvilinear or at an angle to the longitudinal centerline 1205. Portions of the leg regions 1232 may comprise one or more additional extensible stretch zones 1216 and 1218 that are oriented at an angle to the longitudinal centerline 1205 of diaper 1210. Typically, stretch zones 1216 and 1218 may be at an angle of about 45 degrees to about 90 degrees, and preferably at an angle of 45 to 60 degrees, from the longitudinal centerline 1205.

Figure 13:
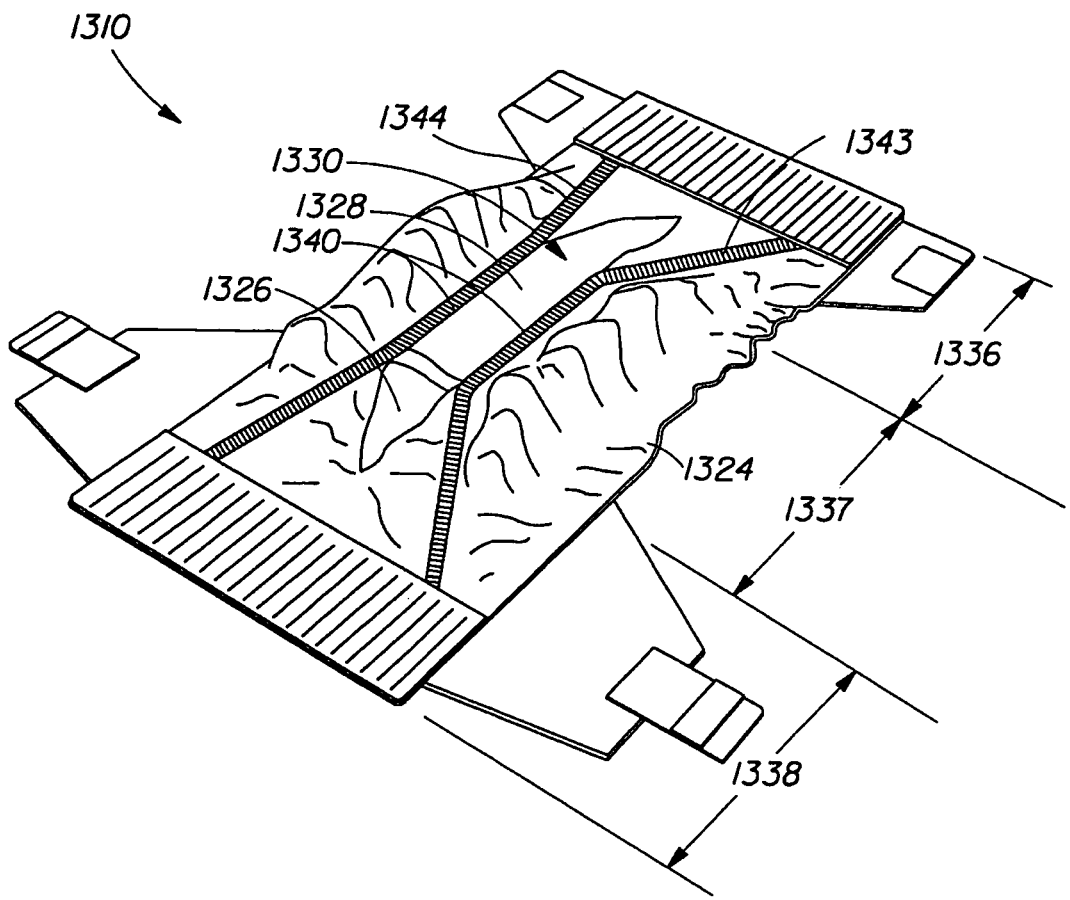
FIG. 13 is a perspective view of a diaper where a stretch zone is used to provide elasticity to a topsheet.

In yet another embodiment of the present invention, the stretch zones described herein can also be provided to a topsheet. For example, diaper 1310 is shown in FIG. 13. Diaper 1310 comprises a topsheet 1324, a backsheet 1326 and core 1328 therebetween. Topsheet 1324 has also been provided with aperture 1330 which has a periphery 1340. As can be seen in FIG. 13, topsheet 1324 is further provided with a pair of laterally opposed stretch zones 1343, 1344 which also comprise a portion of periphery 1340. Stretch zones 1343, 1344 extend from front waist region 1336 through crotch region 1337 to rear waist region 1338. Stretch zones 1343, 1344 provide an elastic resistance causing diaper 1310 to assume a cup-like configuration in the relaxed state shown in FIG. 13. This elastic resistance helps insure desirable bodily contact between topsheet 1324 and a wearer's body. In the preferred embodiment shown in FIG. 13, this bodily contact helps insure that aperture 1330 and topsheet 1326 combine to create a sag tolerable anal cuff to help isolate bodily waste from contact with the wearer's body. Such cuffs are described in greater detail in copending US Patent Application Publication No. 2004/0193134 A1 entitled "Articles with Cuffs", filed in the name of Mueller, et al., published on Sep. 30, 2004.

Diaper Component Description Applicable to all Embodiments of Present Invention

All of the embodiments in FIGS. 1-13 have diaper components which may take any one or more of the materials, designs, and methods of assembly described hereinafter without departing from the scope of the present invention. While any of the article components may be assembled in a variety of well known configurations, exemplary diaper configurations are described generally in U.S. Pat. No. 3,860,003; U.S. Pat. No. 5,151,092; and U.S. Pat. No. 5,221,274; and U.S. Pat. No. 5,554,145; U.S. Pat. No. 5,569,234; U.S. Pat. No. 5,580, 411; and U.S. Pat. No. 6,004,306.

Exemplary breathable materials may include materials such as woven webs, nonwoven webs, composite materials such as film-coated nonwoven webs, microporous films such as manufactured by Mitsui Toatsu Co., of Japan under the designation ESPOIR NO and by Exxon Chemical Co., of Bay City, Tex., under the designation EXXAIRE, and monolithic films such as manufactured by Clopay Corporation, Cincinnati, Ohio under the name HYTREL blend P18-3097 Some breathable composite materials are described in greater detail in U.S. Pat. No. 6,187,696; U.S. Pat. No. 5,938,648; U.S. Pat. No. 5,865,823; and U.S. Pat. No. 5,571,096.

The article may include a structural elastic-like film web is an extensible material that exhibits an elastic-like behavior in the direction of elongation without the use of added elastic materials and is described in more detail in U.S. Pat. No. 5,518,801. In alternate embodiments, the backsheets may comprise elastomeric films, foams, strands, or combinations of these or other suitable materials with nonwovens or synthetic films.

Exemplary absorbent structures for use as the absorbent core are described in U.S. Pat. No. 4,610,678; U.S. Pat. No. 4,673,402; U.S. Pat. No. 4,834,735; U.S. Pat. No. 4,888,231; U.S. Pat. No. 5,137,537; U.S. Pat. No. 5,147,345; U.S. Pat. No. 5,342,338; U.S. Pat. No. 5,260,345; U.S. Pat. No. 5,387, 207; and U.S. Pat. No. 5,625,222.

Suitable absorbent and nonabsorbent sublayers are described in European Patent Application No. EP 0 847 738 A1 and U.S. Pat. No. 5,941,864. Further, the sublayer, or any portion thereof, may include or be coated with a lotion or other known substances to add, enhance or change the performance or other characteristics of the element.

Some exemplary surface fastening systems are disclosed in U.S. Pat. No. 3,848,594; U.S. Pat. No. 4,662,875; U.S. Pat. No. 4,846,815; U.S. Pat. No. 4,894,060; U.S. Pat. No. 4,946, 527; the herein before referenced U.S. Pat. No. 5,151,092; and U.S. Pat. No. 5,221,274. An exemplary interlocking fastening system is disclosed in U.S. Pat. No. 6,432,098. The fastening system may also: provide a means for holding the article in a disposal configuration as disclosed in U.S. Pat. No. 4,963,140; include primary and secondary fastening systems, as disclosed in U.S. Pat. No. 4,699,622; means to reduce shifting of overlapped portions or to improve fit as disclosed in U.S. Pat. No. 5,242,436; means to resist gapping at a wearer's belly as disclosed in U.S. Pat. No. 5,499,978 in U.S. Pat. No. 5,507,736 and in U.S. Pat. No. 5,591,152.

Suitable training pants and pull-on diapers are disclosed in U.S. Pat. No. 5,246,433; U.S. Pat. No. 5,569,234; U.S. Pat.

No. 6,120,487; U.S. Pat. No. 6,120,489;U.S. Pat. No. 4,940,464; and U.S. Pat. No. 5,092,861.

Examples of diapers with elasticized side panels are disclosed in U.S. Pat. No. 4,857,067; U.S. Pat. No. 4,381,781; U.S. Pat. No. 4,938,753; the herein before referenced U.S. Pat. No. 5,151,092; U.S. Pat. No. 5,221,274; U.S. Pat. No. 5,669,897; U.S. Pat. No. 6,004,306, and the aforementioned U.S. Pat. No. 6,300,208.

U.S. Pat. No. 3,860,003 describes a disposable diaper which provides a contractible leg opening having a side flap and one or more elastic members to provide an elasticized leg cuff (a gasketing cuff). U.S. Pat. Nos. 4,808,178 and 4,909,803 describe disposable diapers having "stand-up" elasticized flaps (barrier cuffs) which improve the containment of the leg regions. U.S. Pat. Nos. 4,695,278 and 4,795,454 describe disposable diapers having dual cuffs, including gasketing cuffs and barrier cuffs.

Embodiments of the present invention may also include pockets for receiving and containing waste, spacers which provide voids for waste, barriers for limiting the movement of waste in the article, compartments or voids which accept and contain waste materials or any combinations thereof. Examples of pockets and spacers for use in absorbent products are described in U.S. Pat. No. 5,514,121; U.S. Pat. No. 5,171,236; U.S. Pat. No. 5,397,318; U.S. Pat. No. 5,540,671; U.S. Pat. No. 6,168,584; U.S. Pat. No. 5,306,266; and U.S. Pat. No. 5,997,520. Examples of compartments or voids are disclosed in U.S. Pat. No. 4,968,312; U.S. Pat. No. 4,990,147; U.S. Pat. No. 5,062,840; and U.S. Pat. No. 5,269,755. Examples of suitable transverse barriers are described in U.S. Pat. No. 5,554,142; U.S. Pat. No. 6,010,490; and U.S. Pat. No. 5,653,703. Examples of other structures especially suitable for management of low viscosity feces are disclosed in U.S. Pat. Nos. 5,941,864; 5,977,430 and 6,013,063.

The diaper 10 of FIG. 1 is preferably applied to a wearer by positioning one of the waist regions under the wearer's back and drawing the remainder of the diaper between the wearer's legs so that the other waist region is positioned across the front of the wearer. The fastener elements are then used by the caregiver to join the front and rear waist regions so as to encircle the wearer's waist. The elasticized side panels will typically be extended and tensioned during this operation so as to conform to the size and shape of the wearer. A pant, such as that shown in FIG. 3, may be placed in position on the wearer by inserting the wearer's legs into the leg openings and sliding the pant into position about the wearer's lower torso.

Test Methods

Hysteresis Test for Elastic Properties
Overview
This test measures: a) elastic resistance (load at 25% elongation), b) force relaxation, and c) percent set of an individual stretch zone or an array of stretch zones. The stretch zones can either be intersecting or non-intersecting. Non-intersecting stretch zones can be either parallel or non-parallel. Ideally, the sample dimension should be 2.54 cm wide×5.08 cm long, with the direction of stretch being the long dimension. Furthermore, ideally, the gage length should be 2.54 cm. Because of the variety of patterns that the stretch can be in, it is necessary to define different sample preparation procedures for different classes of stretch zones. Once a sample has been prepared, it is stretched according to a predefined regimen to provide data for property determination.

Apparatus
Tensile Tester: A commercial constant rate of extension tensile tester from Instron Engineering Corp., Canton, Mass. or SINTECH-MTS Systems Corporation, Eden Prairie, Minn. (or a comparable tensile tester) may be suitable. The instrument is interfaced with a computer for controlling the test speed and other test parameters, and for collecting, calculating and reporting the data.
Load Cell Choose the jaws and load cell suitable for the test; the jaws should be wide enough to fit the sample, typically 2.54 cm jaws are used; the load cell is chosen so that the expected tensile response from the sample tested will be between 25% and 75% of the capacity of the load cells or the load range used, typically a 1 kN load cell is used;
Sample Cutter The specific sample cutter is defined by the desired sample width. Suitable cutters are available from Thwing-Albert Instrument Co. of Philadelphia, Pa. For a 2.54 cm wide sample a Model JDC 1-10 is suitable.
Sample Preparation
(i) Sample Preparation for Linear, Non-Intersecting Stretch Zones
Cut a sample that is 2.54 cm wide by 5.08 cm long from within an individual stretch zone. If an individual stretch zone is smaller than these dimensions, the sample should comprise the entire stretch zone. Orient the sample in the jaws to ensure that the sample is stretched in the longitudinal direction of the stretch zone. If the force from an individual stretch zone is too small to measure on the tensile tester, several samples from identical stretch zones taken from multiple products can be pulled collectively in between the grips of the tensile tester, and the data normalized to an individual stretch zone. In the special case when all the stretch zones are uniformly spaced apart and parallel to one another, and also have the same dimensions and basis weight of elastomer, a 2.54 cm sample spanning multiple stretch zones can be tested. The load can then be normalized to an individual stretch zone by dividing the total force by the number of stretch zones.
(ii) Sample Preparation for Non-Linear, Non-Intersecting Stretch Zones
The sample dimensions are 6.3 mm width×5.08 cm length. The length is measured along the curved path. The width of the sample is small so that the curved stretch zone can be approximated as a linear stretch zone. The gage length in the tensile tester is set at 2.54 cm. As mentioned earlier, if it is not possible to obtain a sample of the above dimensions, then the sample dimensions can be decreased to the largest possible and the gage length adjusted according.
(iii) Sample Preparation for an Array of Intersecting Stretch Zones
The test sample is 2.54 cm wide×5.08 cm long. If the array is smaller than these dimensions, the sample should comprise the entire array. The array needs to be pulled in the direction close to the direction of maximum stretch. This can generally be determined by pulling the sample in several directions (e.g., CD, MD and 45 degrees to CD). If such a direction is not easily discernible, the default direction of pull is the cross machine direction.
Method
The hysteresis is measured under standard laboratory conditions (25° C.±2° C. and relative humidity of about 50%±2.0%).
The procedure for determining hysteresis of an elastomeric member involves the following steps:
1. Calibrate the tester according to the manufacturer's instructions.
2. Set the gauge length at 2.54 cm or as appropriate for the sample being tested; set the slack preload at 0.05 N.

3. Place the sample in the flat surface of the jaws such that the longitudinal centerline of the sample is substantially parallel to the gauge length direction.
4. Set the crosshead speed at a constant speed of 25.4 cm/min.
5. Initiate crosshead motion, the tester begins to record load and strain data simultaneously. The hysteresis test specifically involves the following steps:
    a) elongate the sample to 25% strain at a constant rate of 25.4 cm/min-record the force at 25% elongation;
    b) allow the sample to remain at this strain for 2 minutes-record the force at the start and end of the 2 minute period;
    c) return the sample to 0% strain at a constant rate of 25.4 cm/min;
    d) allow sample to remain at this strain for 1 minute; and
    e) elongate the sample to 0.1 N load at a constant rate of 5.08 cm/min-record the strain at 0.1N (i.e., a force sufficient to remove slack but low enough to impart, at most, insubstantial stretch to the sample).

Calculations and Reported Results
1. From the data collected in step 5(a), the load at 25% strain is reported as the elastic resistance of the material.
2. From the data collected in step 5(b), the force relaxation is determined by the load at the beginning and at the end of the 2 minutes hold time using the following formula:

$$\% \text{ Stress Relaxation at time, } t = \frac{\left[\begin{array}{c}(\text{initial load}) - \\ (\text{load at time, } t)\end{array}\right]}{\text{initial load}} \times 100$$

3. From the data collected in step 5(e), the % set is calculated using the following formula:

$$\text{Percent Set} = \left[\left(\frac{\text{Strain Recorded at 5}(e)}{\text{Gage Length}}\right) - 1\right] \times 100$$

4. Report the average results from three replicate samples for each material tested.

Available Strain

Figure 14:
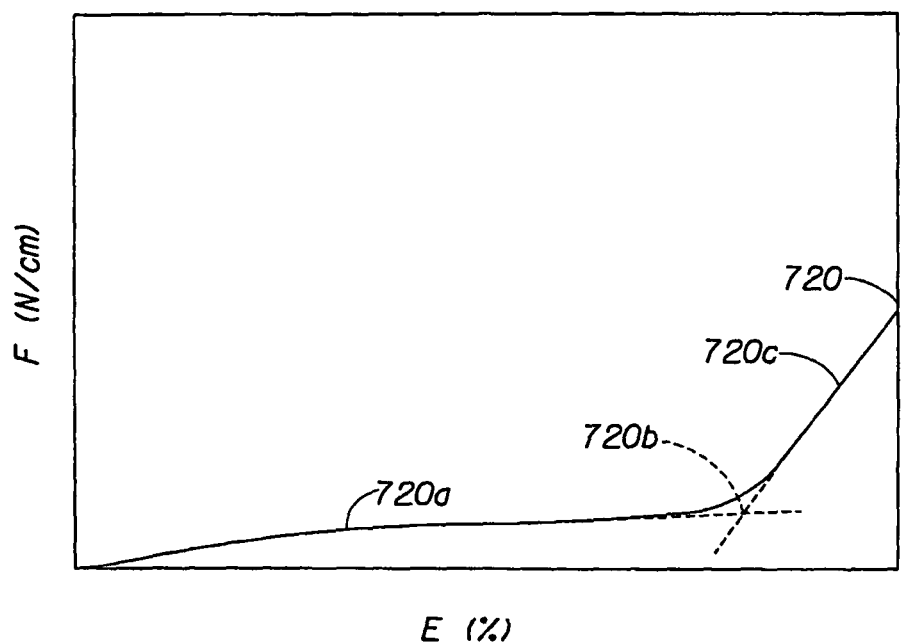
FIG. 14 is an exemplary stress-strain curve showing "Available Strain".

This is intended to determine the Available Strain of a sample. The Available Strain is the point at which there is an inflection in the force—elongation curve, beyond which point there is a rapid increase in the amount of force required to elongate the sample further. An exemplary force (F (N/cm))-elongation (E (%)) curve is shown as FIG. 14. As shown therein, available strain is determined from force elongation curve 720 as the intersection point 720b of linear extrapolations of the stage 1 portion of the curve 720a and the stage 2 portion of the curve 720c.

Method
1. Samples are prepared according to the Hysteresis Test described above.
2. Repeat steps 1-4 of the Hysteresis Test.
3. Initiate crosshead motion. The tester begins to record load versus strain (percent elongation) data simultaneously;
4. Continue elongating the sample until either:
    a) the sample breaks; or
    b) the force limit of the load cell is reached.
5. Plot the force/elongation data to create a curve similar to that shown in FIG. 14.
6. Extrapolate the stage 1 and stage 2 portions as shown to determine the available strain.
7. Report the average results from three replicate samples for each material tested.

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable wearable absorbent article comprising:
    a side panel, the side panel comprising:
        a substrate comprising an inner edge, wherein the inner edge is attached adjacent a side edge of the absorbent article, and wherein the substrate is disposed laterally outboard of the side edge;
        a first array of substantially linear stretch zones disposed on the substrate, wherein each stretch zone is oriented substantially parallel to a lateral centerline of the article, and each stretch zone having a particular width; and
        a second array of stretch zones disposed on the substrate, wherein the second array of stretch zones is disposed longitudinally inboard to the first array of stretch zones, and each stretch zone having a particular width;
        wherein the particular width for each stretch zone of the first array is wider than the particular width of any stretch zone of the second array; and
        wherein each stretch zone includes a thermoplastic elastomeric composition disposed on the substrate, and wherein the thermoplastic elastomeric composition is tackifier free;
    a crotch region including substantially linear and substantially parallel third stretch zones, each third stretch zone oriented substantially perpendicular to the lateral centerline of the absorbent article,
    wherein at least one of the stretch zones of at least one of the first array and the second array is aligned with at least one of the third stretch zones to provide a substantially continuous line of force to encircle a wearer's leg.

2. The disposable wearable absorbent article of claim 1, wherein at least one stretch zone of the second array is oriented substantially parallel to the lateral centerline of the article.

3. The disposable wearable absorbent article of claim 1, wherein each stretch zone of the second array is oriented substantially parallel to the lateral centerline of the article.

4. The disposable wearable absorbent article of claim 1, wherein at least one stretch zone of the second array is oriented at a positive angle with respect to the lateral centerline of the article.

5. The disposable wearable absorbent article of claim 4, wherein the at least one stretch zone of the second array is a substantially linear stretch zone.

6. The disposable wearable absorbent article of claim 4, wherein the at least one stretch zone of the second array is a substantially curved stretch zone.

7. The disposable wearable absorbent article of claim 1, wherein each stretch zone of the second array is oriented at a positive angle with respect to the lateral centerline of the article.

8. The disposable wearable absorbent article of claim 7, wherein each stretch zone of the second array is oriented at substantially the same particular positive angle with respect to a lateral centerline of the article.

9. The disposable wearable absorbent article of claim 7, wherein the second array is a radial array and each stretch zone of the second array radiates out from a point laterally outboard from the second array.

10. The disposable wearable absorbent article of claim 7, wherein each stretch zone of the second array is a substantially linear stretch zone.

11. The disposable wearable absorbent article of claim 10:
including a fourth array of substantially linear stretch zones disposed on the substrate, wherein each stretch zone is oriented at substantially the same particular positive angle with respect to the lateral centerline of the article, and each stretch zone having a particular width;
wherein the fourth array of substantially linear stretch zones is disposed longitudinally inboard to the second array of stretch zones;
wherein the particular width for each stretch zone of the first array is wider than the particular width of any stretch zone of the fourth array; and
wherein the fourth array of substantially linear stretch zones includes a thermoplastic elastomeric composition disposed on the substrate.

12. The disposable wearable absorbent article of claim 10:
including a fourth array of substantially curved stretch zones disposed on the substrate, wherein each stretch zone is oriented at a positive angle with respect to the lateral centerline of the article, and each stretch zone having a particular width;
wherein the fourth array of substantially curved stretch zones is disposed longitudinally inboard to the second array of stretch zones;
wherein the particular width for each stretch zone of the first array is wider than the particular width of any stretch zone of the fourth array; and
wherein the fourth array of substantially curved stretch zones includes a thermoplastic elastomeric composition disposed on the substrate.

13. The disposable wearable absorbent article of claim 7, wherein each stretch zone of the second array is a substantially curved stretch zone.

14. The disposable wearable absorbent article of claim 1, wherein the side panel includes a longitudinally outboard edge and the first array is disposed adjacent to and longitudinally inboard to the longitudinally outboard edge.

15. The disposable wearable absorbent article of claim 1, wherein the first array is disposed adjacent to and laterally inboard to a fastener.

16. The disposable wearable absorbent article of claim 1, wherein each stretch zone of the first array is less than 2 millimeters wide.

17. The disposable wearable absorbent article of claim 1, wherein each stretch zone of the first array is less than 1 millimeter wide.

18. The disposable wearable absorbent article of claim 1, wherein each stretch zone has a thickness between 0.02 millimeters and 5 millimeters.

19. The disposable wearable absorbent article of claim 1, wherein each stretch zone has a basis weight between 20 grams per square meter and 300 grams per square meter.

* * * * *